(12) United States Patent
Carroll

(10) Patent No.: US 8,324,352 B2
(45) Date of Patent: Dec. 4, 2012

(54) ANTI-INFLAMMATORY ANTIBODIES AND USES THEREFOR

(75) Inventor: Elisabeth Carroll, Wellesley, MA (US)

(73) Assignee: DecImmune Therapeutics, Inc., Cambridge, MA (US)

( * ) Notice: Subject to any disclaimer, the term of this patent is extended or adjusted under 35 U.S.C. 154(b) by 0 days.

(21) Appl. No.: 12/962,101

(22) Filed: Dec. 7, 2010

(65) Prior Publication Data

US 2012/0093835 A1     Apr. 19, 2012

Related U.S. Application Data

(60) Provisional application No. 61/275,723, filed on Dec. 7, 2009.

(51) Int. Cl.
*C07K 16/00* (2006.01)
*A61K 39/00* (2006.01)

(52) U.S. Cl. ............... 530/387.1; 530/387.9; 424/139.1

(58) Field of Classification Search .................. None
See application file for complete search history.

(56) References Cited

U.S. PATENT DOCUMENTS

| | | | |
|---|---|---|---|
| 5,859,205 A * | 1/1999 | Adair et al. ............... 530/387.3 |
| 5,928,893 A | 7/1999 | Kang et al. | |
| 7,442,783 B2 | 10/2008 | Carroll et al. | |
| 2003/0099656 A1 | 5/2003 | Patti et al. | |
| 2003/0202975 A1 | 10/2003 | Tedder | |
| 2004/0006208 A1 * | 1/2004 | Karpusas et al. ............. 530/350 |
| 2004/0131607 A1 | 7/2004 | Carroll et al. | |
| 2004/0214272 A1 | 10/2004 | LaRosa et al. | |
| 2005/0276811 A1 | 12/2005 | Carroll et al. | |
| 2008/0262203 A1 | 10/2008 | Clegg et al. | |
| 2009/0176966 A1 | 7/2009 | Carroll et al. | |
| 2010/0136684 A1 | 6/2010 | Carroll et al. | |

FOREIGN PATENT DOCUMENTS

WO     2005085288 A2     9/2005

OTHER PUBLICATIONS

Beiboer et al., "Guided selection of a pan carcinoma specific antibody reveals similar binding characteristics yet structural divergence between the original murine antibody and its human equivalent" J. Mol Biol. (2000) 296: pp. 833-849.*
Eduardo Padlan, "Anatomy of the antibody molecule" Molecular Immun. 31(3) (1994), pp. 169-217.*
Klimka et al., "Human anti-CD30 recombinant antibodies by duided phage antibody selection using cell panning" British Journal of Cancer (2000) 83: pp. 252-260.*
William E. Paul, M.D. "Fundamental Immunology" 3rd Edition, 1993, 292-295.*
Rudikoff et al. "Single amino acid substitution altering antigen-binding specificity" Proc. Natl. Acad. Sci. USA, 79 (Mar. 1982), pp. 1979-1983.*
Zhang, Ming, et al., "Activation of the Lectin Pathway by Natural IgM in a Model of Ischemia/Reperfusion Injury," Journal of Immunology, 177:4272-4734 (2006).
Chan, R.K, et al., "Attenuation of skeletal muscle reperfusion injury with intravenous 12 amino acid peptides that bind to pathogenic IgM," Surgery, pp. 1-8 (2006).
Ahmadi-Yazdi, C., et al., "Attenuation of the Effects of Rat Hemorrhagic Shock with a Reperfusion Injury-Inhibiting Agent Specific to Mice," Shock, 32(3):295-301 (2009).
Haas, M.S., et al., "Blockade of self-reactive IgM significantly reduces injury in a murine model of acute myocardial infarction," Cardiovascular Research, 87:618-627 (2010).
Hofmann, U., et al., "Nothing but natural: targeting natural IgM in ischaemia/reperfusion injury," Cardiovascular Research, 87:589-590 (2010).
Tatlidede, S.H., et al., "Improved Survival of Murine Island Skin Flaps by Prevention of Reperfusion Injury," Plast. Reconstr. Surg., 123(5):1431-1439 (2009).
Suber, F., et al., "Innate response to self-antigen significantly exacerbates burn wound depth," PNAS, 104 (10):3973-3977 (2007).
Huang, J., et al., "Neuronal Protection in Stroke by an sLex-Glycosylated Complement Inhibitory Protein," Science, 285:595-599 (1999).
Zhang, M., et al., "The role of natural IgM in myocardial ischemia-reperfusion injury," J. of Molecular and Cellular Cardiology, 41:62-67 (2006).
Zhang, M, et al., "Identification of the target self-antigens in reperfusion injury," JEM, www.jem.org/cgi/doi/10.1084/jem.20050390, pp. 1-12 (2006).

* cited by examiner

*Primary Examiner* — Maher Haddad
*Assistant Examiner* — James Rogers
(74) *Attorney, Agent, or Firm* — Mahreen Chaudhry Hoda, Esq.; Carolyn S. Elmore, Esq.; Elmore Patent Law Group, P.C.

(57) ABSTRACT

The invention provides antibodies that inhibit activation of complement, which may be used to treat various inflammatory diseases or disorders.

8 Claims, 8 Drawing Sheets

12A6 heavy chain (3609.11.169)

```
<--------------------------------FWR1---------------------------------
caggttactctgaaagagtctggccctgggatattgcagccctcccagaccctcagtctg
 Q   V   T   L   K   E   S   G   P   G   I   L   Q   P   S   Q   T   L   S   L -------------------------------->  <--------CDR1----------->  <----------
acttgttctttctctggattttcactgagc    acttttggtataggagtaggc     tggattcgt
 T   C   S   F   S   G   F   S   L   S    T   F   G   I   G   V   G      W   I   R ------------FWR2----------------->  <-----------CDR2-------------
cagccttcagggaagggtctggagtggctggca    cacatttggtggaatgataataactac
 Q   P   S   G   K   G   L   E   W   L   A    H   I   W   W   N   D   N   N   Y ----------------------->  <------------------FWR3-------------------
tataacacatccctgaagagc    cggctcacaatctccaaggatacctccaacaaccaggta
 Y   N   T   S   L   K   S    R   L   T   I   S   K   D   T   S   N   N   Q   V ----------------------------------------------------------->  <---
ttcctcaagatcgccagtgtggacactgcagatactgccacatactactgtgctcga     gta
 F   L   K   I   A   S   V   D   T   A   D   T   A   T   Y   Y   C   A   R      V -----------------------CDR3---------------------------------------->
ggagggattaacttttctatggactactggggtcaaggaacctcagtcaccgtctcctca   SEQ ID NO: 1
 G   G   I   N   F   S   M   D   Y   W   G   Q   G   T   S   V   T   V   S   S   SEQ ID NO: 2
```

V = 3609.11.169 (96.3%)
D = DSP2.2/DFL16.1 (100%)
J = JH4 (96%)

FIG. 1A

12A6 light chain (8-27)

```
       <---------------------------FWR1----------------------------
       gatattgtgatgacccagtctgcatcatctctggctgtgtctgcaggagaaaaggtcact
        D   I   V   M   T   Q   S   A   S   S   L   A   V   S   A   G   E   K   V   T ---------->    <-----------------------CDR1------------------------->
       atgaactgt      aagtccagtcaaagtgttttatacagttcaaatcagaagaactacttggcc
        M   N   C      K   S   S   Q   S   V   L   Y   S   S   N   Q   K   N   Y   L   A <----------------FWR2----------------------->   <-----CDR2------
       tggtaccagcagaaaccagggcagtctcctaaactgctgatctac   tgggcatccactagg
        W   Y   Q   Q   K   P   G   Q   S   P   K   L   L   I   Y    W   A   S   T   R ------>    <---------------------FWR3--------------------------
       gaatct     ggtgtccctgatcgcttcacaggcagtggatctgggacagatttactcttacc
        E   S      G   V   P   D   R   F   T   G   S   G   S   G   T   D   F   T   L   T ---------------------------------------------------------------->
       atcagcagtgtacaagctgaagacctggcagtttattactgtcatcaatacctctcctcg
        I   S   S   V   Q   A   E   D   L   A   V   Y   Y   C   H   Q   Y   L   S   S <---------------CDR3--------------->
       tggacgttcggtggaggcaccaagctggaaatcaaacgg    SEQ ID NO: 7
        W   T   F   G   G   G   T   K   L   E   I   K   R    SEQ ID NO: 8
```

21G6 heavy chain (J558.35)

```
<---------------------------FWR1------------------------------
caggtccagctgcaggagtctggggctgaactggtgaagcctggggcttcagtgaagttg
 Q  V  Q  L  Q  E  S  G  A  E  L  V  K  P  G  A  S  V  K  L ------------------------------>  <----CDR1-------> <-----FWR2-------
tcctgcaaggcttctggctacaccttcacc   agctactatatgtac    tgggtgaagcagagg
 S  C  K  A  S  G  Y  T  F  T     S  Y  Y  M  Y     W  V  K  Q  R ---------------------------> <---------------CDR2----------------
cctggacaaggccttgagtggattggg   gggattaatcctagcaatggtggtactaacttc
 P  G  Q  G  L  E  W  I  G     G  I  N  P  S  N  G  G  T  N  F ------------------->  <----------------------FWR3-----------------
aatgagaagttcaagagc    aaggccacactgactgtagacaaatcctccagcacagcctac
 N  E  K  F  K  S      K  A  T  L  T  V  D  K  S  S  T  A  Y -----------------------------------------------------> <-------
atgcaactcagcagcctgacatctgaggactctgcggtctattactgtacaaga   tggggt
 M  Q  L  S  S  L  T  S  E  D  S  A  V  Y  Y  C  T  R    W  G -----------------------------CDR3------------------------------->
tacgacagggagtggtttgcttactggggccaagggactctggtcactgtctctgca    SEQ ID NO: 13
 Y  D  R  E  W  F  A  Y  W  G  Q  G  T  L  V  T  V  S  A     SEQ ID NO: 14
```

V = J558.35 (97.9%)
D = DSP2.6/DSP2.4/DSP2.3 (100%)
J = JH3 (100%)

FIG. 2A

21G6 light chain (hf24)

```
<--------------------------FWR1-----------------------------
gatattgtgatgactcaggctgcaccctctgtacctgtcactcctggagagtcagtatcc
 D  I  V  M  T  Q  A  A  P  S  V  P  V  T  P  G  E  S  V  S ----------> <-------------------CDR1----------------------> <----
atctcctgc   aggtctagtaagagtctcctgcatagtaatggcaacacttacttgtat   tgg
 I  S  C     R  S  S  K  S  L  L  H  S  N  G  N  T  Y  L  Y     W ------------FWR2-----------------------> <------CDR2----------->
ttcctgcagaggccaggccagtctcctcaggtcctgatatat   cggatgtccaaccttgcctca
 F  L  Q  R  P  G  Q  S  P  Q  V  L  I  Y     R  M  S  N  L  A  S <------------------------FWR3---------------------
ggagtcccagacaggttcagtggcagtgggtcaggaactgctttcacactgagaatc
 G  V  P  D  R  F  S  G  S  G  T  A  F  T  L  R  I ----------------------------------------------------------->
agtagagtggaggctgaggatgtgggtgtttattactgtatgcaacatctagaatatcca
 S  R  V  E  A  E  D  V  G  V  Y  Y  C  M  Q  H  L  E  Y  P <------------CDR3------------------->
ttcacgttcggctcggggacaaagttggaaataaaacgg    SEQ ID NO: 19
 F  T  F  G  S  G  T  K  L  E  I  K  R     SEQ ID NO: 20
```

ANTI-INFLAMMATORY ANTIBODIES AND USES THEREFOR

CROSS REFERENCE TO RELATED APPLICATIONS

This present application claims the benefit of priority to U.S. Provisional Patent Application Ser. No. 61/275,723, filed Dec. 7, 2009. The entire contents of this application is hereby expressly incorporated by reference.

1. BACKGROUND OF THE INVENTION

Acute inflammatory responses can result from a wide range of diseases and naturally occurring events such as stroke and myocardial infarction. Common medical procedures can also lead to localized and systemic inflammation. Left untreated inflammation can result in significant tissue loss and may ultimately lead to multi-system failure and death. Interfering with the inflammatory response after injury may be one method to reduce tissue loss. Accumulating evidence supports a major role for the serum innate response or complement system in inflammation.

Recent studies implicate an important role for natural antibody and the classical pathway of complement in the inflammatory response. It has been determined that ischemia-reperfusion injury can be initiated by clonally specific natural IgM that activates the classical pathway of complement. (Zhang et al. (2004) Proc. Natl. Acad. Sci. 101(11):3886-3891.) These studies have led to the identification of pathogenic IgMs and, in turn, the identification of self-peptides that bind natural IgM, described in U.S. Pat. No. 7,442,783. U.S. Pat. No. 7,442,783 describes a conserved region within type II NMHC proteins (corresponding to amino acids 592-603 of Mouse NMHC-IIB (the N2 self-peptide; SEQ ID NO:33)) representing the major epitope for binding of natural IgM following ischmeia in an intestinal model.

Inflammatory diseases or disorders are potentially life-threatening, costly, and affect a large number of people every year. Thus, effective treatments of inflammatory diseases or disorders are needed.

2. SUMMARY OF THE INVENTION

In one aspect, the invention features isolated antibodies, in particular IgGs, that bind to the N2 self-peptide and inhibit inflammation. The antibodies are capable of inhibiting activation of complement, thereby inhibiting an immune response to the N2 self-peptide. In another embodiment, the antibody has a light chain variable region comprising the amino acid sequence shown as SEQ ID NO: 8 or 20. In another embodiment, the antibody has a heavy chain variable region comprising the amino acid sequence shown as SEQ ID NO: 2 or 14. In another embodiment, the antibody is produced by the hybridoma deposited with the American Type Culture Collection (ATCC), 10801 University Blvd., Manassas, VA 20110-2209 on Jul. 30, 2008 having Accession Number PTA-9392. In yet another embodiment, the antibody is produced by the hybridoma deposited with the American Type Culture Collection (ATCC), 10801 University Blvd., Manassas, VA 20110-2209 on Jul. 30, 2008 having Accession Number PTA-9393.

In another aspect, the invention features nucleic acids encoding the anti-inflammatory antibodies, as well as vectors and host cells expressing the same.

In a further aspect, the invention features methods of inhibiting activation of an immune response to the N2 self-peptide in a subject by administering to the subject an anti-inflammatory antibody described herein. In a further aspect, the invention features methods of treating an inflammatory disease, such as e.g., ischemia-reperfusion injury, in a subject by administering to the subject a pharmaceutical composition comprising an isolated anti-inflammatory antibody as described herein.

Other features and advantages of the invention will be apparent based on the following Detailed Description and Claims.

3. BRIEF DESCRIPTION OF THE DRAWINGS

FIG. 1 shows antibody heavy and light chain sequences of murine B-cell hybridoma 12A6 (PTA-9392). (A) shows the $IgG^{12A6}$ (or 12A6 IgG) heavy chain nucleic acid sequence (SEQ ID NO: 1) and the amino acid sequence corresponding to the heavy chain sequence of SEQ ID NO: 1 (SEQ ID NO: 2). Framework regions (FVWR) and complementarity-determining regions (CDR) are indicated above the nucleotides. FIG. 1A discloses the CDR1, CDR2 and CDR 3 domain nucleotide and encoded amino acid sequences as SEQ ID NOS 3-6 and 25-26 respectively, in order of appearance. (B) shows the $IgG^{12A6}$ (or 12A6 IgG) light chain nucleic acid sequence (SEQ ID NO: 7) and the amino acid sequence corresponding to the light chain sequence of SEQ ID NO: 7 (SEQ ID NO: 8). Framework regions (FVWR) and complementarity-determining regions (CDR) are indicated above the nucleotides. FIG. 1B discloses the CDR1, CDR2 and CDR3 domain nucleotide and encoded amino acid sequences as SEQ ID NOS 9-12 and 27-28 respectively, in order of appearance.

FIG. 2 shows antibody heavy and light chain sequences of murine B-cell hybridoma 21G6 (PTA-9393). (A) shows the $IgG^{21G6}$ (or 21G6 IgG) heavy chain nucleic acid sequence (SEQ ID NO: 13) and the amino acid sequence corresponding to the heavy chain sequence of SEQ ID NO: 13 (SEQ ID NO: 14). Framework regions (FVWR) and complementarity-determining regions (CDR) are indicated above the nucleotides. FIG. 2A discloses the CDR1, CDR2 and CDR3 domain nucleotide and encoded amino acid sequences as SEQ ID NOS 15-18 and 29-30 respectively, in order of appearance. (B) shows the $IgG^{21G6}$ (or 21G6 IgG) light chain nucleic acid sequence (SEQ ID NO: 19) and the amino acid sequence corresponding to the light chain sequence of SEQ ID NO: 19 (SEQ ID NO: 20). Framework regions (FVWR) and complementarity-determining regions (CDR) are indicated above the nucleotides. FIG. 2B discloses the CDR1, CDR2 and CDR3 domain nucleotide and encoded amino acid sequences as SEQ ID NOS 21-24 and 31-32 respectively, in order of appearance.

Figure 3:
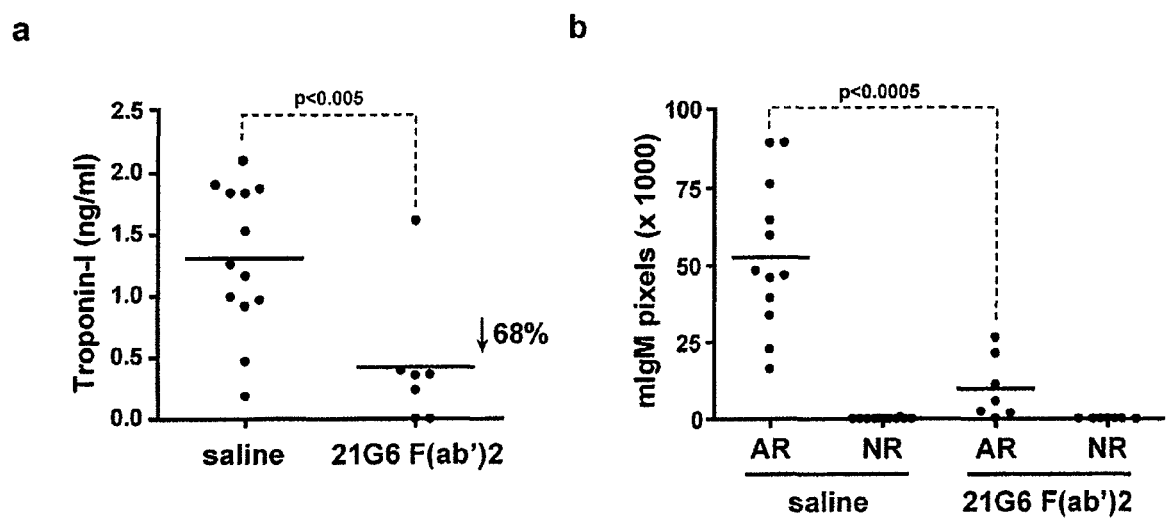
FIG. 3 shows that murine anti-N2 mAb (anti-N2 F(ab')$_2$ antibody (21G6)) inhibits inflammation following myocardial infarction.

4. DETAILED DESCRIPTION 4.1. Definitions:

For convenience, certain terms employed in the specification, examples, and appended claims are provided. Unless defined otherwise, all technical and scientific terms used herein have the same meaning as commonly understood by one of ordinary skill in the art to which this invention belongs.

"A" and "an" are used herein to refer to one or to more than one (i.e., to at least one) of the grammatical object of the article. By way of example, "an element" means one element or more than one element.

"Amino acid" is used herein to refer to either natural or synthetic amino acids, including glycine and D or L optical isomers, and amino acid analogs and peptidomimetics.

"Antibody" is used herein to refer to binding molecules including immunoglobulin molecules, antibody fragments, and immunologically active portions of immunoglobulin molecules, i.e., molecules that contain an antigen-binding site. Immunoglobulin molecules useful in the invention can be of any class (e.g., IgG, IgE, IgM, IgD, and IgA) or subclass. Native antibodies and immunoglobulins are usually heterotetrameric glycoproteins of about 150,000 daltons, composed of two identical light chains and two identical heavy chains. Each heavy chain has at one end a variable domain followed by a number of constant domains. Each light chain has a variable domain at one end and a constant domain at its other end. Antibodies include, but are not limited to, polyclonal, monoclonal, bispecific, chimeric, partially or fully humanized antibodies, fully human antibodies (i.e., generated in a transgenic mouse expressing human immunoglobulin genes), camel antibodies, and anti-idiotypic antibodies. An antibody, or generally any molecule, "binds specifically" to an antigen (or other molecule) if the antibody binds preferentially to the antigen, and, e.g., has less than about 30%, preferably 20%, 10%, or 1% cross-reactivity with another molecule. The terms "antibody" and "immunoglobulin" are used interchangeably.

"Antibody fragment" is used herein to refer to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, minibody, Fc, Fd fragments, and single chain antibodies. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

"Antigen-binding site" is used herein to refer to the variable domain of a heavy chain associated with the variable domain of a light chain.

"Bind" or "binding" are used herein to refer to detectable relationships or associations (e.g. biochemical interactions) between molecules.

"Cells" or "host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Comprise" and "comprising" are used in the inclusive, open sense, meaning that additional elements may be included.

A "consensus" sequence refers to the sequence formed from the most frequently occurring amino acids (or nucleotides) in a family of related sequences (See. e.g., Winnaker, From Genes to Clones, 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an immunoglobulin can be preferably replaced with another amino acid residue from the same side chain family. Alternatively, in another embodiment, mutations can be introduced randomly along all or part of an immunoglobulin coding sequence, such as by saturation mutagenesis, and the resultant mutants can be screened for biological activity.

"Interaction" refers to a physical association between two or more molecules, e.g., binding. The interaction may be direct or indirect.

"Inflammatory disease" is used herein to refer to a disease or disorder that is caused or contributed to by a complicated set of functional and cellular adjustments involving acute or chronic changes in microcirculation, movement of fluids, and influx and activation of inflammatory cells (e.g., leukocytes) and complement, and included autoimmune diseases. Examples of such diseases and conditions include, but are not limited to: reperfusion injury, ischemia injury, stroke, autoimmune hemolytic anemia, idiopathic thrombocytopenic purpura, rheumatoid arthritis, celiac disease, hyper-IgM immunodeficiency, arteriosclerosis, coronary artery disease, sepsis, myocarditis, encephalitis, transplant rejection, hepatitis, thyroiditis (e.g. Hashimoto's thyroiditis, Graves disease), osteoporosis, polymyositis, dermatomyositis, Type I diabetes, gout, dermatitis, alopecia greata, systemic lupus erythematosus, lichen sclerosis, ulcerative colitis, diabetic retinopathy, pelvic inflammatory disease, periodontal disease, arthritis, juvenile chronic arthritis (e.g. chronic iridocyclitis), psoriasis, osteoporosis, nephropathy in diabetes mellitus, asthma, pelvic inflammatory disease, chronic inflammatory liver disease, chronic inflammatory lung disease, lung fibrosis, liver fibrosis, rheumatoid arthritis, chronic inflammatory liver disease, chronic inflammatory lung disease, lung fibrosis, liver fibrosis, Crohn's disease, ulcerative colitis, burns, and other acute and chronic inflammatory diseases of the Central Nervous System (CNS; e.g. multiple sclerosis), gastrointestinal system, the skin and associated structures, the immune system, the hepato-biliary system, or any site in the body where pathology can occur with an inflammatory component.

An "isolated" molecule, e.g., an isolated antibody, refers to a condition of being separate or purified from other molecules present in the natural environment.

"Natural IgM" is used herein to refer to an IgM antibody that is naturally produced in a mammal (e.g., a human). They have a pentameric ring structure wherein the individual monomers resemble IgGs thereby having two light (κ or λ) chains and two heavy (μ) chains. Further, the heavy chains contain an additional $C_H4$ domain. The monomers form a pentamer by disulfide bonds between adjacent heavy chains. The pentameric ring is closed by the disulfide bonding between a J chain and two heavy chains. Because of its high number of antigen binding sites, an IgG antibody is an effective agglutinator of antigen. Production of natural IgM antibodies in a subject are important in the initial activation of B-cells, macrophages, and the complement system. IgM is the first immunoglobulin synthesized in an antibody response. IgMs are described in U.S. Pat. No. 7,442,783, the entire contents of which are specifically incorporated herein by reference.

"Nucleic acid" is used herein to refer to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

"Operatively linked" is used herein to refer to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

"Patient", "subject" or "host" are used herein to refer to either a human or a non-human mammal.

"Peptide" is used herein to refer to a polymer of amino acids of relatively short length (e.g. less than 50 amino acids). The polymer may be linear or branched, it may comprise modified amino acids, and it may be interrupted by non-amino acids. The term also encompasses an amino acid polymer that has been modified; for example, disulfide bond formation, glycosylation, lipidation, acetylation, phosphorylation, or any other manipulation, such as conjugation with a labeling component.

"Promoter" is used herein to refer to a minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the of a polynucleotide sequence. Both constitutive and inducible promoters, are included in the invention (see e.g., Bitter et al., *Methods in Enzymology* 153:516-544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention. Tissue-specific regulatory elements may be used. Including, for example, regulatory elements from genes or viruses that are differentially expressed in different tissues.

"Specifically binds" or "immunospecifically binds" is used herein to refer to the interaction between two molecules to form a complex that is relatively stable under physiologic conditions. The term is used herein in reference to various molecules, including, for example, the interaction of an antibody and an antigen (e.g. a peptide). Specific binding can be characterized by a dissociation constant of at least about $1\times10^{-6}$ M, generally at least about $1\times10^{-7}$ M, usually at least about $1\times10^{-8}$ M, and particularly at least about $1\times10^{-9}$ M or $1\times10^{-10}$ M or greater. Methods for determining whether two molecules specifically bind are well known and include, for example, equilibrium dialysis, surface plasmon resonance, and the like.

"Stringency hybridization" or "hybridizes under low stringency, medium stringency, high stringency, or very high stringency conditions" is used herein to describes conditions for hybridization and washing. Guidance for performing hybridization reactions can be found in Current Protocols in *Molecular Biology*, John Wiley & Sons, N.Y. (1989), 6.3.1-6:3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences and the percent homology between two sequences is a function of the number of conserved positions shared by the sequences, taking into account the number of gaps, and the length of each gap, which need to be introduced for optimal alignment of the two sequences. The comparison of sequences and determination of percent identity and/or homology between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available on the world wide web with the extension gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available on the world wide web with the extension gcg.com), using a NWS-gapdna CMP matrix and a gap weight of 40, 50, 60, 70; or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frame shift gap penalty of 5.

The percent identity and/or homology between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Treating" is used herein to refer to any treatment of, or prevention of, or inhibition of a disorder or disease in a subject and includes by way of example: (a) preventing the disease or disorder from occurring in a subject that may be predisposed to the disease or disorder, but has not yet been diagnosed as having it; (b) inhibiting the disease or disorder, i.e., arresting its progression; or (c) relieving or ameliorating the disease or disorder, i.e., causing regression. Thus, treating as used herein includes, for example, repair and regeneration of damaged or injured tissue or cells at the site of injury or prophylactic treatments to prevent damage, e.g., before surgery.

"Vector" as used herein refers to a nucleic acid molecule, which is capable of transporting another nucleic acid to which it has been operatively linked and can include a plasmid, cosmid, or viral vector. One type of preferred vector is an episome, i.e., a nucleic acid capable of extra-chromosomal replication. Preferred vectors are those capable of autonomous replication and/or expression of nucleic acids to which they are linked. Vectors may be capable of directing the expression of genes to which they are operatively linked. A vector may also be capable of integrating into the host DNA. In the present specification, "plasmid" and "vector" are used interchangeably as a plasmid (a circular arrangement of double stranded DNA) is the most commonly used form of a vector. However, the invention is intended to include such other forms of vectors which serve equivalent functions and which become known in the art subsequently hereto. Viral vectors include, e.g., replication defective retroviruses, adenoviruses and adeno-associated viruses.

4.2 Anti-inflammatory Antibodies

The present invention is based, at least in part, on the identification of antibodies that bind to the N2 self peptide and inhibit inflammation. Certain antibodies may be obtained from a hybridoma that has been deposited with the American Type Culture Collection and provided Accession Number PTA-9392 ($IgG^{12A6}$) or PTA-9393 ($IgG^{21G6}$).

In one aspect, the present invention provides an isolated antibody that specifically binds to an amino acid sequence comprising the N2 self-peptide of Mouse NMHC-IIB (592-603) (LMKNMDPLNDNV (N2; SEQ ID NO:33)). In another aspect, the anti-inflammatory antibody specifically binds to an amino acid sequence encoded by a nucleic acid comprising YTN ATG AAR AAY ATG GAY CCN YTN AAY GAY AAY GTN (SEQ ID NO: 34), where an "R" corresponds to a base that may be a A or G; a "Y" corresponds to a base that may be a C or T; and an "N" corresponds to a base that may be an A, C, G or T, and is capable of inhibiting inflammation in a subject to whom the antibody is administered.

N2 is a self-antigen and in particular an ischemic antigen, or an antigen expressed or exposed on damaged ischemic tissue. Natural IgM recognizes and binds N2 expressed or exposed on damaged tissue, and in particular damaged ischemic tissue, and thereby initiates inflammation by activating complement in the classical pathway. The anti-inflammatory antibodies described herein compete with natural IgM antibodies in binding self-antigen, thereby titrating out self-antigen available to bind IgM and activate complement. When administered to a subject, the anti-inflammatory antibodies described herein inhibit activation of complement, thereby inhibiting inflammation.

The present invention encompasses antibodies that immunospecifically bind to the N2 self-peptide having heavy chain variable region ("VH") comprising one or more of the VH complementarity determining regions ("CDRs") shown in FIGS. 1 and 2. The present invention also encompasses antibodies that immunospecifically bind to the N2 self-peptide having a light chain variable region ("VL") comprising one or more of the VL complementarity determining regions shown in FIGS. 1 and 2.

$IgG^{12A6}$ (12A6 IgG)

The nucleotide sequence of the heavy chain variable region of the IgG produced from hybridoma PTA-9392, $IgG^{12A6}$ (also referred to as 12A6 IgG) is shown in FIG. 1A (SEQ ID NO: 1), and the amino acid sequence is also shown in FIG. 1A (SEQ ID NO: 2). The CDR1 domain of the heavy chain variable region corresponds to a region of SEQ ID NO: 2 (shown as SEQ ID NO: 4), which is encoded by a region of SEQ ID NO: 1 (shown as SEQ ID NO: 3), and the CDR2 domain of the heavy chain variable region corresponds to a region of SEQ ID NO: 2 (shown as SEQ ID NO: 6), which is encoded by a region of SEQ ID NO: 1 (shown as SEQ ID NO: 5). The CDR3 domain of the heavy chain variable region corresponds to a region of SEQ ID NO: 2 (shown as SEQ ID NO: 26), which is encoded by a region of SEQ ID NO: 1 (shown as SEQ ID NO: 25) in FIG. 1A.

The nucleotide sequence of the light chain variable region of $IgG^{12A6}$ is shown in FIG. 1B (SEQ ID NO: 7), and the amino acid sequence is also shown in FIG. 1B (SEQ ID NO: 8). The CDR1 domain of the light chain variable region corresponds to a region of SEQ ID NO: 8 (shown as SEQ ID NO: 10), which is encoded by a region of SEQ ID NO: 7 (shown as SEQ ID NO: 9), and the CDR2 domain of the light chain variable region corresponds to a region of SEQ ID NO: 8 (shown as SEQ ID NO: 12), which is encoded by a region of SEQ ID NO: 7 (shown as SEQ ID NO: 11) in FIG. 1B. The CDR3 domain of the light chain variable region corresponds to a region of SEQ ID NO: 8 (shown as SEQ ID NO: 28), which is encoded by a region of SEQ ID NO: 7 (shown as SEQ ID NO: 27) in FIG. 1B.

Due to the degeneracy of the genetic code, other nucleotide sequences can encode the amino acid sequences listed herein.

The nucleic acid compositions of the present invention, while often in a native sequence (except for modified restriction sites and the like), from either cDNA, genomic or mixtures may be mutated, in accordance with standard techniques. For coding sequences, these mutations, may affect the amino acid sequence as desired. In particular, nucleotide sequences substantially identical to or derived from native V, D, J, constant, switches and other such sequences described herein are contemplated.

For example, an isolated nucleic acid can comprise an IgG$^{12A6}$ (or 12A6 IgG) heavy chain variable region nucleotide sequence having a nucleotide sequence as shown in FIG. 1A (SEQ ID NO: 1), or a sequence, which is at least 80%, 90%, 95%, 96%, 97%, 98%, or 99% identical to SEQ ID NO: 1. A nucleic acid molecule may comprise the heavy chain CDR1 nucleotide sequence of SEQ ID NO: 3, or a portion thereof. Further, the nucleic acid molecule may comprise the heavy chain CDR2 nucleotide sequence of SEQ ID NO: 5, or a portion thereof. Further, the nucleic acid molecule may comprise the heavy chain CDR3 nucleotide sequence of SEQ ID NO: 25, or a portion thereof. In an exemplary embodiment, the nucleic acid molecule comprises a heavy chain CDR1 nucleotide sequence of SEQ ID NO: 3, or portion thereof, and a heavy chain CDR2 nucleotide sequence of SEQ ID NO: 5, or portion thereof, and a heavy chain CDR3 nucleotide sequence of SEQ ID NO: 25, or portion thereof. The nucleic acid molecules of the present invention may comprise heavy chain sequences, e.g. SEQ ID NO: 1, SEQ ID NO: 3, SEQ ID NO: 5, SEQ ID NO: 25, or combinations thereof, or encompass nucleotides having at least 80%, 90%, 95%, 96%, 97%, 98%, and 99% sequence identity to SEQ ID NOs: 1, 3, 5, or 25. Further, the nucleic acid molecules of the present invention may comprise heavy chain sequences, which hybridize under stringent conditions, e.g. low, medium, high or very high stringency conditions, to SEQ ID NOs: 1, 3, 5, or 25.

In another embodiment, the invention features nucleic acid molecules having at least 80%, 90%, 95%, 96%, 97%, 98%, and 99% sequence identity with a nucleic acid molecule encoding a heavy chain polypeptide, e.g., a heavy chain polypeptide of SEQ ID NOs: 2, 4, 6, or 26. The invention also features nucleic acid molecules which hybridize to nucleic acid sequences encoding a heavy chain variable region of an antibody or portion thereof, e.g., a heavy chain variable region of SEQ ID NO: 2, 4, 6, or 26.

In another embodiment, the isolated nucleic acid encodes an IgG$^{12A6}$ (12A6 IgG) light chain variable region nucleotide sequence having a nucleotide sequence as shown in FIG. 1B (SEQ ID NO: 7), or a sequence at least 80%, 90%, 95%, 96%, 97%, 98%, 99% identical to SEQ ID NO: 7. The nucleic acid molecule may comprise the light chain CDR1 nucleotide sequence of SEQ ID NO: 9, or a portion thereof. In another embodiment, the nucleic acid molecule may comprise the light chain CDR2 nucleotide sequence of SEQ ID NO: 11, or a portion thereof. In another embodiment, the nucleic acid molecule may comprise the light chain CDR3 nucleotide sequence of SEQ ID NO: 27, or a portion thereof. In an exemplary embodiment, the nucleic acid molecule comprises a light chain CDR1 nucleotide sequence of SEQ ID NO: 9, or portion thereof, and a light chain CDR2 nucleotide sequence of SEQ ID NO: 11, or portion thereof, and a light chain CDR3 nucleotide sequence of SEQ ID NO: 27, or portion thereof. The nucleic acid molecules of the present invention may comprise light chain sequences, e.g. SEQ ID NOs: 7, 9, 11, 27, or combinations thereof, or encompass nucleotides having at least 80%, 90%, 95%, 96%, 97%, 98%, and 99% sequence identity to SEQ ID NOs: 7, 9, 11, or 27. Further nucleic acid molecules may comprise light chain sequences, which hybridize under stringent conditions, e.g. low, medium, high or very high stringency conditions, to SEQ ID NOs: 7, 9, 11, or 27.

Nucleic acid molecules can have at least 80%, 90%, 95%, 96%, 97%, 98% or 99% sequence identity with a nucleic acid molecule encoding a light chain polypeptide, e.g., a light chain polypeptide of SEQ ID NOs: 8, 10, 12, or 28. The invention also features nucleic acid molecules which hybridize to a nucleic acid sequence encoding a light chain variable region of an antibody or portion thereof, e.g., a light chain variable region of SEQ ID NOs: 8, 10, 12, or 28.

In another embodiment, the invention provides an isolated nucleic acid encoding a heavy chain CDR1 domain comprising the amino acid sequence of SEQ ID NO: 4, or a fragment or modified form thereof. This nucleic acid can encode only the CDR1 region or can encode an entire antibody heavy chain variable region or a fragment thereof. For example, the nucleic acid can encode a heavy chain variable region having a CDR2 domain comprising the amino acid sequence of SEQ ID NO: 6. In yet another embodiment, the invention provides an isolated nucleic acid encoding a heavy chain CDR2 domain comprising the amino acid sequence of SEQ ID NO: 6, or a fragment or modified form thereof. This nucleic acid can encode only the CDR2 region or can encode an entire antibody heavy chain variable region or a fragment thereof. For example, the nucleic acid can encode a light chain variable region having a CDR1 domain comprising the amino acid sequence of SEQ ID NO: 4.

In still another embodiment, the invention provides an isolated nucleic acid encoding a light chain CDR1 domain comprising the amino acid sequence of SEQ ID NO: 10, or a fragment or modified form thereof. This nucleic acid can encode only the CDR1 region or can encode an entire antibody light chain variable region. For example, the nucleic acid can encode a light chain variable region having a CDR2 domain comprising the amino acid sequence of SEQ ID NO: 12. The isolated nucleic acid can also encode a light chain CDR2 domain comprising the amino acid sequence of SEQ ID NO: 12, or a fragment or modified form thereof. This nucleic acid can encode only the CDR2 region or can encode an entire antibody light chain variable region. For example, the nucleic acid can encode a light chain variable region having a CDR1 domain comprising the amino acid sequence of SEQ ID NO: 10.

The nucleic acid encoding the heavy or light chain variable region can be of murine or human origin, or can comprise a combination of murine and human amino acid sequences. For example, the nucleic acid can encode a heavy chain variable region comprising the CDR1 of SEQ ID NO: 2 (SEQ ID NO: 4) and/or the CDR2 of SEQ ID NO: 2 (SEQ ID NO: 6), and/or the CDR3 of SEQ ID NO: 2 (SEQ ID NO: 26) and a human framework sequence. In addition, the nucleic acid can encode a light chain variable region comprising the CDR1 of SEQ ID NO: 8 (SEQ ID NO: 10) and/or the CDR2 of SEQ ID NO: 8 (SEQ ID NO: 12), and/or the CDR3 of SEQ ID NO: 2 (SEQ ID NO: 26) and a human framework sequence. The invention further encompasses vectors containing the above-described nucleic acids and host cells containing the expression vectors.

The invention also features polypeptides and fragments of the IgG$^{12A6}$ heavy chain variable regions and/or light chain variable regions. Any of the polypeptides encoded by nucleic acids described herein are within the scope of the invention. In exemplary embodiments, the isolated polypeptides comprise, for example, the amino acid sequences of SEQ ID NOs: 8, 10, 12, 28, or fragments or combinations thereof; or SEQ ID NO: 2, 4, 6, 26, or fragments or combinations thereof. The polypeptides of the present invention include polypeptides having at least, but not more than 20, 10, 5, 4, 3, 2, or 1 amino acid that differs from SEQ ID NOs: 8, 10, 12, 28, 2, 4, 6, or 26. Exemplary polypeptides are polypeptides that retain biological activity, e.g., the ability to bind the N2 self-peptide, and/or the ability to inhibit activation of complement. In another embodiment, the polypeptides comprise polypeptides having at least 80%, 90%, 95%, 96%, 97%, 98%, and 99% sequence identity with a light chain variable region, or portion thereof, e.g. a light chain variable region polypeptide of SEQ ID NOs: 8, 10, 12, or 28. In another embodiment, the polypeptides comprise polypeptides having at least 80%, 90%, 95%, 96%, 97%, 98%, and 99% sequence identity with a heavy chain variable region, or portion thereof, e.g. a heavy chain variable region polypeptide of SEQ ID NOs: 2, 4, 6, or 26. In another embodiment, the invention features a polypeptide comprising the amino acid sequence of SEQ ID NO: 8 and SEQ ID NO: 2, further comprising an IRES sequence.

In one embodiment of the present invention, antibodies that immunospecifically bind to the N2 self-peptide comprise a VH CDR1 having the amino acid sequence of SEQ ID NO:4. In another embodiment, antibodies that immunospecifically bind to the N2 self-peptide comprise a VH CDR2 having the amino acid sequence of SEQ ID NO:6. In another embodiment, antibodies that immunospecifically bind to the N2 self-peptide comprise a VH CDR3 having the amino acid sequence of SEQ ID NO:26.

In another embodiment, antibodies that immunospecifically bind to the N2 self-peptide comprise a VH CDR1 having the amino acid sequence of SEQ ID NO:4 and a VH CDR2 having the amino acid sequence of SEQ ID NO:6. In another embodiment, antibodies that immunospecifically bind to the N2 self-peptide comprise a VH CDR1 having the amino acid sequence of SEQ ID NO:4 and a VH CDR3 having the amino acid of SEQ ID NO:26. In yet another embodiment, antibodies that immunospecifically bind to the N2 self-peptide comprise a VH CDR2 having the amino acid sequence of SEQ ID NO:6 and a VH CDR3 having the amino acid of SEQ ID NO:26. In another embodiment, antibodies that immunospecifically bind to the N2 self-peptide comprise a VH CDR1 having the amino acid sequence of SEQ ID NO:4, a VH CDR2 having the amino acid sequence of SEQ ID NO:6, and a VH CDR3 having the amino acid of SEQ ID NO:26.

In one embodiment of the present invention, antibodies that immunospecifically bind to an N2 self-peptide comprise a VL CDR1 having the amino acid sequence of SEQ ID NO:10. In another embodiment, antibodies that immunospecifically bind to the N2 self-peptide comprise a VL CDR2 having the amino acid sequence of SEQ ID NO:12. In another embodiment, antibodies that immunospecifically bind to the N2 self-peptide comprise a VL CDR3 having the amino acid sequence of SEQ ID NO:28.

In another embodiment, antibodies that immunospecifically bind to the N2 self-peptide comprise a VL CDR1 having the amino acid sequence of SEQ ID NO:10 and a VL CDR2 having the amino acid sequence of SEQ ID NO:12. In another embodiment, antibodies that immunospecifically bind to the N2 self-peptide comprise a VL CDR1 having the amino acid sequence of SEQ ID NO:10 and a VL CDR3 having the amino acid of SEQ ID NO:28. In another embodiment, antibodies that immunospecifically bind to the N2 self-peptide comprise a VL CDR2 having the amino acid sequence of SEQ ID NO:12 and a VL CDR3 having the amino acid of SEQ ID NO:28. In yet another embodiment, antibodies that immunospecifically bind to the N2 self-peptide comprise a VL CDR1 having the amino acid sequence of SEQ ID NO:10, a VL CDR2 having the amino acid sequence of SEQ ID NO:12, and a VL CDR3 having the amino acid of SEQ ID NO:28.

The present invention also provides antibodies comprising one or more VH CDRs and one or more VL CDRs as shown in FIGS. 1 and 2. In particular, the invention provides for an antibody comprising a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof of the VH CDRs and VL CDRs shown in FIGS. 1 and 2.

In one embodiment, an antibody of the invention comprises a VH CDR1 having the amino acid sequence of SEQ ID NO:4 and a VL CDR1 having the amino acid sequence of SEQ ID NO:10. In another embodiment, an antibody of the present invention comprises a VH CDR1 having the amino acid sequence of SEQ ID NO:4 and a VL CDR2 having the amino acid sequence of SEQ ID NO:12. In another embodiment, an antibody of the present invention comprises a VH CDR1 having the amino acid sequence of SEQ ID NO:4 and a VL CDR3 having the amino acid sequence of SEQ ID NO:28.

In another embodiment, an antibody of the present invention comprises a VH CDR2 having the amino acid sequence of SEQ ID NO:6 and a VL CDR1 having the amino acid sequence of SEQ ID NO:10. In another embodiment, an antibody of the present invention comprises a VH CDR2 having the amino acid sequence of SEQ ID NO:6 and a VL CDR2 having the amino acid sequence of SEQ ID NO:12. In another embodiment, an antibody of the present invention comprises a VH CDR2 having the amino acid sequence of SEQ ID NO:6 and a VL CDR3 having the amino acid sequence of SEQ ID NO:28.

In another embodiment, an antibody of the present invention comprises a VH CDR3 having the amino acid sequence of SEQ ID NO:14, and a VL CDR1 having the amino acid sequence of SEQ ID NO:10. In another embodiment, an antibody of the present invention comprises a VH CDR3 having the amino acid sequence of SEQ ID NO:26 and a VL CDR2 having the amino acid sequence of SEQ ID NO:12. In a preferred embodiment, an antibody of the present invention comprises a VH CDR3 having the amino acid sequence of SEQ ID NO:14 and a VL CDR3 having the amino acid sequence of SEQ ID NO:28.

IgG$^{21G6}$ (21G6 IgG)

The nucleotide sequence of the heavy chain variable region of the IgG produced from hybridoma PTA-9393, IgG$^{21G6}$ (also referred to as 21G6 IgG) is shown in FIG. 2A (SEQ ID NO: 13), and the amino acid sequence is also shown in FIG. 2A (SEQ ID NO: 14). The CDR1 domain of the heavy chain variable region corresponds to a region of SEQ ID NO: 14 (shown as SEQ ID NO: 16), which is encoded by a region of SEQ ID NO: 13 (shown as SEQ ID NO: 15), and the CDR2 domain of the heavy chain variable region corresponds to a region of SEQ ID NO: 14 (shown as SEQ ID NO: 18), which is encoded by a region of SEQ ID NO: 13 (shown as SEQ ID NO: 17). The CDR3 domain of the heavy chain variable region corresponds to a region of SEQ ID NO: 14 (shown as SEQ ID NO: 30), which is encoded by a region of SEQ ID NO: 13 (shown as SEQ ID NO: 29).

The nucleotide sequence of the light chain variable region of IgG$^{21G6}$ is shown in FIG. 2B (SEQ ID NO: 19), and the amino acid sequence is also shown in FIG. 2B (SEQ ID NO: 20). The CDR1 domain of the light chain variable region corresponds to a region of SEQ ID NO: 20 (SEQ ID NO: 22), which is encoded by a region of SEQ ID NO: 19 (SEQ ID NO: 21), and the CDR2 domain of the light chain variable region corresponds to a region of SEQ ID NO: 20 (SEQ ID NO: 24), which is encoded by a region of SEQ ID NO: 19 (SEQ ID NO: 23). The CDR3 domain of the light chain variable region corresponds to a region of SEQ ID NO: 20 (shown as SEQ ID NO: 32), which is encoded by a region of SEQ ID NO: 19 (shown as SEQ ID NO: 31).

Due to the degeneracy of the genetic code, other nucleotide sequences can encode the amino acid sequences listed herein.

The nucleic acid compositions of the present invention, while often in a native sequence (except for modified restriction sites and the like), from either cDNA, genomic or mixtures may be mutated, in accordance with standard techniques. For coding sequences, these mutations, may affect the amino acid sequence as desired. In particular, nucleotide sequences substantially identical to or derived from native V, D, J, constant, switches and other such sequences described herein are contemplated.

For example, an isolated nucleic acid can comprise an IgG$^{21G6}$ (or 21G6 IgG) heavy chain variable region nucleotide sequence as shown in FIG. 2A (SEQ ID NO: 13), or a sequence, which is at least 80%, 90%, 95%, 96%, 97%, 98%, or 99% identical to SEQ ID NO: 13. In certain embodiments, the nucleotides at positions 19-21 of SEQ ID NO: 13 are selected from the group consisting of TCT, TCC, TCA, TCG, CCT, CCC, CCA, CCG, AGT, and AGC. A nucleic acid molecule may comprise the heavy chain CDR1 nucleotide sequence of SEQ ID NO: 15, or a portion thereof. Further, the nucleic acid molecule may comprise the heavy chain CDR2 nucleotide sequence of SEQ ID NO: 17, or a portion thereof. Further, the nucleic acid molecule may comprise the heavy chain CDR3 nucleotide sequence of SEQ ID NO: 29, or a portion thereof. In an exemplary embodiment, the nucleic acid molecule comprises a heavy chain CDR1 nucleotide sequence of SEQ ID NO: 15, or portion thereof, and a heavy chain CDR2 nucleotide sequence of SEQ ID NO: 17, or portion thereof, and a heavy chain CDR3 nucleotide sequence of SEQ ID NO: 29, or portion thereof. The nucleic acid molecules of the present invention may comprise heavy chain sequences, e.g. SEQ ID NO: 13, SEQ ID NO: 15, SEQ ID NO: 17, SEQ ID NO: 29, or combinations thereof, or encompass nucleotides having at least 80%, 90%, 95%, 96%, 97%, 98%, and 99% sequence identity to SEQ ID NOs: 13, 15, 17, or 29. Further, the nucleic acid molecules of the present invention may comprise heavy chain sequences, which hybridize under stringent conditions, e.g. low, medium, high or very high stringency conditions, to SEQ ID NOs: 13, 15, 17, or 29.

In another embodiment, the invention features nucleic acid molecules having at least 80%, 90%, 95%, 96%, 97%, 98%, and 99% sequence identity with a nucleic acid molecule encoding a heavy chain polypeptide, e.g., a heavy chain polypeptide of SEQ ID NOs: 14, 16, 18, or 30. In certain embodiments, the amino acid sequence at position 7 of SEQ ID NO: 14 comprises a serine or a proline. The invention also features nucleic acid molecules which hybridize to nucleic acid sequences encoding a heavy chain variable region of an antibody or portion thereof, e.g., a heavy chain variable region of SEQ ID NO: 14, 16, 18, or 30.

In another embodiment, the isolated nucleic acid encodes an IgG$^{21G6}$ (21G6 IgG) light chain variable region nucleotide sequence having a nucleotide sequence as shown in FIG. 2B (SEQ ID NO: 19), or a sequence at least 80%, 90%, 95%, 96%, 97%, 98%, 99% identical to SEQ ID NO: 19. The nucleic acid molecule may comprise the light chain CDR1 nucleotide sequence of SEQ ID NO: 21, or a portion thereof. In another embodiment, the nucleic acid molecule may comprise the light chain CDR2 nucleotide sequence of SEQ ID NO: 23, or a portion thereof. In another embodiment, the nucleic acid molecule may comprise the light chain CDR3 nucleotide sequence of SEQ ID NO: 31, or a portion thereof. In an exemplary embodiment, the nucleic acid molecule comprises a light chain CDR1 nucleotide sequence of SEQ ID NO: 21, or portion thereof, and a light chain CDR2 nucleotide sequence of SEQ ID NO: 23, or portion thereof, and a light chain CDR3 nucleotide sequence of SEQ ID NO: 31, or portion thereof. The nucleic acid molecules of the present invention may comprise light chain sequences, e.g. SEQ ID NOs: 19, 21, 23, 31, or combinations thereof, or encompass nucleotides having at least 80%, 90%, 95%, 96%, 97%, 98%, and 99% sequence identity to SEQ ID NOs: 19, 21, 23, or 31. Further nucleic acid molecules may comprise light chain sequences, which hybridize under stringent conditions, e.g. low, medium, high or very high stringency conditions, to SEQ ID NOs: 19, 21, 23, or 31.

Nucleic acid molecules can have at least 80%, 90%, 95%, 96%, 97%, 98% or 99% sequence identity with a nucleic acid molecule encoding a light chain polypeptide, e.g., a light chain polypeptide of SEQ ID NOs: 20, 22, 24, or 32. The invention also features nucleic acid molecules which hybridize to a nucleic acid sequence encoding a light chain variable region of an antibody or portion thereof, e.g., a light chain variable region of SEQ ID NOs: 20, 22, 24, or 32.

In another embodiment, the invention provides an isolated nucleic acid encoding a heavy chain CDR1 domain comprising the amino acid sequence of SEQ ID NO: 16, or a fragment or modified form thereof. This nucleic acid can encode only the CDR1 region or can encode an entire antibody heavy chain variable region or a fragment thereof. For example, the nucleic acid can encode a heavy chain variable region having a CDR2 domain comprising the amino acid sequence of SEQ ID NO: 18. In yet another embodiment, the invention provides an isolated nucleic acid encoding a heavy chain CDR3 domain comprising the amino acid sequence of SEQ ID NO: 30, or a fragment or modified form thereof. This nucleic acid can encode only the CDR2 region or can encode an entire antibody heavy chain variable region or a fragment thereof. For example, the nucleic acid can encode a light chain variable region having a CDR1 domain comprising the amino acid sequence of SEQ ID NO: 16.

In still another embodiment, the invention provides an isolated nucleic acid encoding a light chain CDR1 domain comprising the amino acid sequence of SEQ ID NO: 22, or a fragment or modified form thereof. This nucleic acid can encode only the CDR1 region or can encode an entire antibody light chain variable region. For example, the nucleic acid can encode a light chain variable region having a CDR2 domain comprising the amino acid sequence of SEQ ID NO: 24. The isolated nucleic acid can also encode a light chain CDR3 domain comprising the amino acid sequence of SEQ ID NO: 32, or a fragment or modified form thereof. This nucleic acid can encode only the CDR2 region or can encode an entire antibody light chain variable region. For example, the nucleic acid can encode a light chain variable region having a CDR1 domain comprising the amino acid sequence of SEQ ID NO: 22.

The nucleic acid encoding the heavy or light chain variable region can be of murine or human origin, or can comprise a combination of murine and human amino acid sequences. For example, the nucleic acid can encode a heavy chain variable region comprising the CDR1 of SEQ ID NO: 14 (SEQ ID NO: 16) and/or the CDR2 of SEQ ID NO: 14 (SEQ ID NO: 18), and/or the CDR3 of SEQ ID NO: 14 (SEQ ID NO: 30) and a human framework sequence. In addition, the nucleic acid can encode a light chain variable region comprising the CDR1 of SEQ ID NO: 20 (SEQ ID NO: 22) and/or the CDR2 of SEQ ID NO: 20 (SEQ ID NO: 24), and/or the CDR3 of SEQ ID NO: 20 (SEQ ID NO: 32) and a human framework sequence. The invention further encompasses vectors containing the above-described nucleic acids and host cells containing the expression vectors.

The invention also features polypeptides and fragments of the IgG$^{21G6}$ heavy chain variable regions and/or light chain variable regions. Any of the polypeptides encoded by nucleic acids described herein are within the scope of the invention. In exemplary embodiments, the isolated polypeptides comprise, for example, the amino acid sequences of SEQ ID NOs: 20, 22, 24, or 32, or fragments or combinations thereof; or SEQ ID NO: 14, 16, 18, or 30, or fragments or combinations thereof. The polypeptides of the present invention include polypeptides having at least, but not more than 20, 10, 5, 4, 3, 2, or 1 amino acid that differs from SEQ ID NOs: 20, 22, 24, 32, 14, 16, 18, or 30. Exemplary polypeptides are polypeptides that retain biological activity, e.g., the ability to bind to the N2 self-peptide and the ability to inhibit activation of complement and/or inhibit inflammation. In another embodiment, the polypeptides comprise polypeptides having at least 80%, 90%, 95%, 96%, 97%, 98%, and 99% sequence identity with a light chain variable region, or portion thereof, e.g. a light chain variable region polypeptide of SEQ ID NOs: 20, 22, 24, or 32. In another embodiment, the polypeptides comprise polypeptides having at least 80%, 90%, 95%, 96%, 97%, 98%, and 99% sequence identity with a heavy chain variable region, or portion thereof, e.g. a heavy chain variable region polypeptide of SEQ ID NOs: 14, 16, 18, or 30. In another embodiment, the invention features a polypeptide comprising the amino acid sequence of SEQ ID NO: 20 and SEQ ID NO: 14, further comprising an IRES sequence.

In one embodiment of the present invention, antibodies that immunospecifically bind to the N2 self-peptide comprise a VH CDR1 having the amino acid sequence of SEQ ID NO:16. In another embodiment, antibodies that immunospecifically bind to the N2 self-peptide comprise a VH CDR2 having the amino acid sequence of SEQ ID NO:18. In another embodiment, antibodies that immunospecifically bind to the N2 self-peptide comprise a VH CDR3 having the amino acid sequence of SEQ ID NO:30.

In another embodiment, antibodies that immunospecifically bind to the N2 self-peptide comprise a VH CDR1 having the amino acid sequence of SEQ ID NO:16 and a VH CDR2 having the amino acid sequence of SEQ ID NO:18. In another embodiment, antibodies that immunospecifically bind to the N2 self-peptide comprise a VH CDR1 having the amino acid sequence of SEQ ID NO:16 and a VH CDR3 having the amino acid of SEQ ID NO:30. In yet another embodiment, antibodies that immunospecifically bind to the N2 self-peptide comprise a VH CDR2 having the amino acid sequence of SEQ ID NO:18 and a VH CDR3 having the amino acid of SEQ ID NO:30. In another embodiment, antibodies that immunospecifically bind to the N2 self-peptide comprise a VH CDR1 having the amino acid sequence of SEQ ID NO:16, a VH CDR2 having the amino acid sequence of SEQ ID NO:18, and a VH CDR3 having the amino acid of SEQ ID NO:30.

In one embodiment of the present invention, antibodies that immunospecifically bind to an N2 self-peptide comprise a VL CDR1 having the amino acid sequence of SEQ ID NO:22. In another embodiment, antibodies that immunospecifically bind to the N2 self-peptide comprise a VL CDR2 having the amino acid sequence of SEQ ID NO:24. In another embodiment, antibodies that immunospecifically bind to the N2 self-peptide comprise a VL CDR3 having the amino acid sequence of SEQ ID NO:32.

In another embodiment, antibodies that immunospecifically bind to the N2 self-peptide comprise a VL CDR1 having the amino acid sequence of SEQ ID NO:22 and a VL CDR2 having the amino acid sequence of SEQ ID NO:24. In another embodiment, antibodies that immunospecifically bind to the N2 self-peptide comprise a VL CDR1 having the amino acid sequence of SEQ ID NO:22 and a VL CDR3 having the amino acid of SEQ ID NO:32. In another embodiment, antibodies that immunospecifically bind to the N2 self-peptide comprise a VL CDR2 having the amino acid sequence of SEQ ID NO:24 and a VL CDR3 having the amino acid of SEQ ID NO:32. In yet another embodiment, antibodies that immunospecifically bind to the N2 self-peptide comprise a VL CDR1 having the amino acid sequence of SEQ ID NO:22, a VL CDR2 having the amino acid sequence of SEQ ID NO:24, and a VL CDR3 having the amino acid of SEQ ID NO:32.

In one embodiment, an antibody of the invention comprises a VH CDR1 having the amino acid sequence of SEQ ID NO:16 and a VL CDR1 having the amino acid sequence of SEQ ID NO:22. In another embodiment, an antibody of the present invention comprises a VH CDR1 having the amino acid sequence of SEQ ID NO:16 and a VL CDR2 having the amino acid sequence of SEQ ID NO:24. In another embodiment, an antibody of the present invention comprises a VH CDR1 having the amino acid sequence of SEQ ID NO:16 and a VL CDR3 having the amino acid sequence of SEQ ID NO:32.

In another embodiment, an antibody of the present invention comprises a VH CDR2 having the amino acid sequence of SEQ ID NO:18 and a VL CDR1 having the amino acid sequence of SEQ ID NO:22. In another embodiment, an antibody of the present invention comprises a VH CDR2 having the amino acid sequence of SEQ ID NO:18 and a VL CDR2 having the amino acid sequence of SEQ ID NO:24. In another embodiment, an antibody of the present invention comprises a VH CDR2 having the amino acid sequence of SEQ ID NO:18 and a VL CDR3 having the amino acid sequence of SEQ ID NO:32.

In another embodiment, an antibody of the present invention comprises a VH CDR3 having the amino acid sequence of SEQ ID NO:30, and a VL CDR1 having the amino acid sequence of SEQ ID NO:22. In another embodiment, an antibody of the present invention comprises a VH CDR3 having the amino acid sequence of SEQ ID NO:30 and a VL CDR2 having the amino acid sequence of SEQ ID NO:24. In a preferred embodiment, an antibody of the present invention comprises a VH CDR3 having the amino acid sequence of SEQ ID NO:30 and a VL CDR3 having the amino acid sequence of SEQ ID NO:32.

4.3 Modified Anti-inflammatory Antibodies

Other anti-N2 anti-inflammatory antibodies having the properties described herein may be produced. Methods of producing antibodies are well known in the art and may be used for producing modified anti-N2 anti-inflammatory antibodies.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., Nature (1990) 348:552-554, complete $V_H$ and $V_L$ domains of an antibody, joined by a flexible (Gly$_4$-Ser)$_3$ (SEQ ID NO: 35) linker can be used to produce a single chain antibody which can render the display package separable based on antigen affinity. Isolated scFV antibodies immunoreactive with the antigen can subsequently be formulated into a pharmaceutical preparation for use in the subject method.

An antibody of the present invention can be one in which the variable region, or a portion thereof, e.g., the complementarity determining regions (CDR or CDRs), are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention. Any modification is within the scope of the invention so long as the antibody has at least one antigen binding portion.

Chimeric antibodies (e.g. mouse-human monoclonal antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184, 187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl. Cancer Inst. 80:1553-1559).

A chimeric antibody can be further humanized by replacing sequences of the Fv variable region which are not directly involved in antigen binding with equivalent sequences from human Fv variable regions. General methods for generating humanized antibodies are provided by Morrison, S. L., 1985, Science 229:1202-1207 by Oi et al., 1986, BioTechniques 4:214, and by Queen et al. U.S. Pat. Nos. 5,585,089, 5,693, 761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody can then be cloned into an appropriate expression vector. Suitable humanized antibodies can alternatively be produced by CDR substitution. U.S. Pat. No. 5,225,539; Jones et al. 1986 Nature 321:552-525; Verhoeyan et al. 1988 Science 239:1534; and Beidler et al. 1988 J. Immunol. 141:4053-4060.

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

A humanized or CDR-grafted antibody will have at least one or two but generally all recipient CDRs (of heavy and/or light immunoglobulin chains) replaced with a donor CDR. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework can be a naturally-occurring (e.g., a human) framework or a consensus framework, or a sequence about 85% or higher, preferably 90%, 95%, 99% or higher identical thereto.

All of the CDRs of a particular antibody may be replaced with at least a portion of a non-human CDR or only some of the CDRs may be replaced with non-human CDRs. It is only necessary to replace the number of CDRs required for binding of the humanized antibody to the Fc receptor.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, a humanized antibody will have framework residues identical to the donor framework residue or to another amino acid other than the recipient framework residue. As another example, in a humanized antibody having mouse CDRs, amino acids located in the human framework region can be replaced with the amino acids located at the corresponding positions in the mouse antibody. Another example of a humanized antibody is a murine monoclonal antibody having a murine variable region but modified to have a human Fc region. Such substitutions are known to improve binding of humanized antibodies to the antigen in some instances.

Additionally, amino acid substitutions, deletions or additions may be made to the antibodies described herein to inhibit or block inflammation. For example, asparagine at position 297 of the IgG constant region may be substituted by alanine (N297A) to reduce glycosylation and thereby ability to activate complement and bind Fc receptor. (See e.g., Leatherbarrow R J, et al. (1985) Effector functions of a monoclonal aglycosylated mouse IgG2a: binding and activation of complement component C1 and interaction with human monocyte Fc receptor. (Translated from eng) Mol Immunol 22(4):407-415; Tao M H & Morrison S L (1989) Studies of aglycosylated chimeric mouse-human IgG. Role of carbohydrate in the structure and effector functions mediated by the human IgG constant region. (Translated from eng) J Immunol 143(8):2595-2601; and Kabat (1987) Sequences of Proteins of Immunological Interest (In: US Department of Human Services). The contents of each of these references are expressly incorporated herein by reference.

Antibody fragments of the invention can be obtained using conventional procedures known to one of skill in the art. For example, digestion of an antibody with pepsin yields F(ab')2 fragments and multiple small fragments. Mercaptoethanol reduction of an antibody yields individual heavy and light chains. Digestion of an antibody with papain yields individual Fab fragments and the Fc fragment.

The invention also features a method of making an anti-inflammatory antibody. The method includes: altering the sequence of an antibody, e.g., by substitution or deletion of one or more residues of a non-conserved region, a domain or residue disclosed herein, and testing the altered polypeptide for binding to N2 and inhibiting activation of complement.

In certain embodiments, the modified antibody may comprise at least the CDR1 region of SEQ ID NO: 8 (SEQ ID NO: 10), or antigen binding portions thereof, and/or at least the CDR2 region of SEQ ID NO: 8 (SEQ ID NO: 12), or antigen binding portions thereof. In another embodiment, the modified antibody may comprise at least the CDR1 region of SEQ ID NO: 2 (SEQ ID NO: 4), or antigen binding portions thereof, and/or at least the CDR2 region of SEQ ID NO: 2 (SEQ ID NO: 6), or antigen binding portions thereof. In an exemplary embodiment, the modified antibody comprises the CDR1 region of SEQ ID NO: 8 (SEQ ID NO: 10) and the CDR2 region of SEQ ID NO: 8 (SEQ ID NO: 12) or antigen binding portions thereof. In another exemplary embodiment, the modified antibody comprises the CDR1 region of SEQ ID NO: 2 (SEQ ID NO: 4) and the CDR2 region of SEQ ID NO: 2 (SEQ ID NO: 6) or antigen binding portions thereof. The modified antibody may also comprise the CDR1 region of SEQ ID NO: 8 (SEQ ID NO: 10) and the CDR2 region of SEQ ID NO: 8 (SEQ ID NO: 12) and the modified antibody comprises the CDR1 region of SEQ ID NO: 2 (SEQ ID NO: 4) and the CDR2 region of SEQ ID NO: 2 (SEQ ID NO: 6) or antigen binding portions thereof.

In certain embodiments, the modified antibody may comprise at least the CDR1 region of SEQ ID NO: 20 (SEQ ID NO: 22), or antigen binding portions thereof, and/or at least the CDR2 region of SEQ ID NO: 20 (SEQ ID NO: 24), or antigen binding portions thereof. In another embodiment, the modified antibody may comprise at least the CDR1 region of SEQ ID NO: 14 (SEQ ID NO: 16), or antigen binding portions thereof, and/or at least the CDR2 region of SEQ ID NO: 14 (SEQ ID NO: 18), or antigen binding portions thereof. In an exemplary embodiment, the modified antibody comprises the CDR1 region of SEQ ID NO: 20 (SEQ ID NO: 22) and the CDR2 region of SEQ ID NO: 20 (SEQ ID NO: 24) or antigen binding portions thereof. In another exemplary embodiment, the modified antibody comprises the CDR1 region of SEQ ID NO: 14 (SEQ ID NO: 16) and the CDR2 region of SEQ ID NO: 14 (SEQ ID NO: 18) or antigen binding portions thereof. The modified antibody may also comprise the CDR1 region of SEQ ID NO: 20 (SEQ ID NO: 22) and the CDR2 region of SEQ ID NO: 20 (SEQ ID NO: 24) and the modified antibody comprises the CDR1 region of SEQ ID NO: 14 (SEQ ID NO: 16) and the CDR2 region of SEQ ID NO: 14 (SEQ ID NO: 18) or antigen binding portions thereof.

The modified antibody can be a human antibody having a binding affinity to the N2 self-antigen, similar, e.g., greater than, less than, or equal to, the binding affinity of the antibody produced by the hybridoma deposited, pursuant to the Budapest Treaty, with the American Type Culture Collection (ATCC), 10801 University Blvd., Manassas, VA 20110-2209 on Jul. 30, 2008, having the Accession Number PTA-9392 or the Accession Number PTA-9393. In another embodiment, the antibody can be a non-human antibody, e.g., a cow, goat, mouse, rat, sheep, pig, or rabbit. In an exemplary embodiment, the non-human antibody is a murine antibody. The antibody may also be a recombinant antibody. In an exemplary embodiment, the antibody is a humanized antibody. The modified antibody may be an IgG antibody. In another embodiment, the isolated antibody possess the same antigenic specificity as the antibody produced by the hybridoma deposited with the ATCC on Jul. 30, 2008, having the Accession Number PTA-9392 or Accession Number PTA-9393. In certain embodiments, the antibody possessing the same antigenic specificity as the antibody produced by the hybridoma deposited with the ATCC on Jul. 30, 2008, having the Accession Number PTA-9392 or Accession Number PTA-9393 wherein the antibody is a human antibody, humanized antibody, chimeric antibody or an antibody fragment of any of thereof.

Antibodies may be modified, for example to increase solubility and/or facilitate purification, identification, detection, and/or structural characterization. Exemplary modifications, include, for example, addition of: glutathione S-transferase (GST), protein A, protein G, calmodulin-binding peptide, thioredoxin, maltose binding protein, HA, myc, poly-arginine, poly-His, poly-His-Asp or FLAG fusion proteins and tags. In various embodiments, an antibody may comprise one or more heterologous fusions. For example, peptides may contain multiple copies of the same fusion domain or may contain fusions to two or more different domains. The fusions may occur at the N-terminus of the peptide, at the C-terminus of the peptide, or at both the N- and C-terminus of the peptide. It is also within the scope of the invention to include linker sequences between a peptide of the invention and the fusion domain in order to facilitate construction of the fusion protein or to optimize protein expression or structural constraints of the fusion protein. In another embodiment, the peptide may be constructed so as to contain protease cleavage sites between the fusion peptide and peptide of the invention in order to remove the tag after protein expression or thereafter. Examples of suitable endoproteases, include, for example, Factor Xa and TEV proteases.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments, which may subsequently be annealed to generate a chimeric gene sequence (see, for example, Current Protocols in Molecular Biology, eds. Ausubel et al., John Wiley & Sons: 1992).

Antibodies may be chemically modified based on linkage to a polymer. The polymer is typically water soluble so that the antibody to which it is attached does not precipitate in an aqueous environment, such as a physiological environment. The polymer may have a single reactive group, such as an active ester for acylation or an aldehyde for alkylation, so that the degree of polymerization may be controlled. A preferred reactive aldehyde is polyethylene glycol propionaldehyde, which is water stable, or mono C1-C10 alkoxy or aryloxy derivatives thereof (see U.S. Pat. No. 5,252,714). The polymer may be branched or unbranched. Preferably, for therapeutic use of the end-product preparation, the polymer will be pharmaceutically acceptable. The water soluble polymer, or mixture thereof if desired, may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

4.4 Antibody Preparations

The data obtained from the cell culture assays and animal studies can be used in formulating a range of dosage for use in humans. The dosage of an antibody lies preferably within a range of circulating concentrations that include the $ED_{50}$ with little or no toxicity. The dosage may vary within this range depending upon the dosage form employed and the route of administration utilized. For any antibody used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In another embodiment, a single bolus of an antibody is administered prior to, contemporaneously with, or subsequent to a tissue injury. Typically a single dose injection will be a few hours, a few days or a few weeks after tissue injury. The present invention is based in part upon the discovery that an anti-inflammatory antibody inhibits or prevents reperfusion injury. A single unit dosage delivery can be immediately adjacent to the site of injury or can be, for example, to a vessel that drains or flows to the site of injury.

An anti-inflammatory antibody is administered initially at a point in time prior to the time of damage of the target organ or tissue. This may be a useful approach in subjects who are determined to be at risk for reperfusion injury, such as those with a history of reperfusion injury or those about to undergo surgery.

In yet another embodiment, a single bolus of an anti-inflammatory antibody can be followed by subsequent administrations of an anti-inflammatory antibody as continuous infusions or additional single bolus deliveries. The anti-inflammatory antibody may be administer in sequential exposures over a period of hours, days, weeks, months or years. In addition, it is contemplated that additional therapeutic agents can be combined with, administered prior to or subsequent to administration of an anti-inflammatory antibody. Other therapeutic agents that may be administered with an anti-inflammatory antibody include, but are not limited to, anti-coagulation agents and complement inhibitors.

The subject anti-inflammatory antibodies may be provided in pharmaceutically acceptable carriers or formulated for a variety of modes of administration, including systemic and topical or localized administration. Techniques and formulations generally may be found in Remmington's Pharmaceutical Sciences, Meade Publishing Co., Easton, Pa. In certain embodiments, the antibody is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, compositions of the invention are formulated into ointments, salves, gels, or creams as generally known in the art.

The pharmaceutical compositions according to the invention are prepared by bringing an anti-inflammatory antibody into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories and including, for example, alginate based pH dependent release gel caps. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or by several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. As discussed above, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference.

In one embodiment, the invention provides a pharmaceutical composition useful for administering an antibody-binding peptide to a subject in need of such treatment. "Administering" the pharmaceutical composition of the invention may be accomplished by any means known to the skilled artisan. Preferably a "subject" refers to a mammal, most preferably a human.

The anti-inflammatory antibody can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water. Where the disease or disorder is a gastrointestinal disorder oral formulations or suppository formulations are preferred.

Sterile injectable solutions can be prepared by incorporating a antibody-binding peptide in the required amount (e.g., about 10 μg to about 10 mg/kg) in an appropriate solvent and then sterilizing, such as by sterile filtration. Further, powders can be prepared by standard techniques such as freeze drying or vacuum drying.

In another embodiment, an anti-inflammatory antibody is prepared with a biodegradable carrier for sustained release characteristics for either sustained release in the GI tract or for target organ implantation with long term active agent release characteristics to the intended site of activity. Biodegradable polymers include, for example, ethylene vinyl acetate, polyanhydrides, polyglycolic acids, polylactic acids, collagen, polyorthoesters, and poly acetic acid. Liposomal formulation can also be used.

Another means of delivering anti-inflammatory antibody is by delivering host cells that express antibody-binding peptides to a site or tissue in need of repair. Alternatively, the cells may be delivered in conjunction with various delivery vehicles, including biocompatible biodegradable or non-biodegradable sponges (e.g., collagen, or other extracellular matrix materials), cotton, polyglycolic acid, cat gut sutures, cellulose, gelatin, dextran, polyamide, a polyester, a polystyrene, a polypropylene, a polyacrylate, a polyvinyl, a polycarbonate, a polytetrafluoroethylene, or a nitrocellulose compound formed into a three-dimensional structure (see, for example, U.S. Pat. No. 5,858,721 to Naughton et al., the disclosure of which is incorporated herein by reference).

Any route of administration compatible with the active principle can be used. The preferred is parenteral administration, such as subcutaneous, intramuscular or intravenous injection. The dose of the active ingredient to be administered depends on the basis of the medical prescriptions according to age, weight and the individual response of the patient.

The daily non-weighted dosage for the patient can be between about 2.5-5.0 mg/Kg, e.g., about 2.5-3.0 mg/Kg, about 3.0-3.5 mg/Kg, about 3.5-4.0 mg/Kg, about 4.0-4.5 mg/Kg, and about 4.5-5.0 mg/Kg.

The pharmaceutical composition for parenteral administration can be prepared in an injectable form comprising the active principle and a suitable vehicle. Vehicles for the parenteral administration are well known in the art and comprise, for example, water, saline solution, Ringer solution and/or dextrose. The vehicle can contain small amounts of excipients in order to maintain the stability and isotonicity of the pharmaceutical preparation. The preparation of the cited solutions can be carried out according to the ordinary modalities.

The present invention has been described with reference to the specific embodiments, but the content of the description comprises all modifications and substitutions, including conservative amino acid substitutions, which can be brought by a person skilled in the art without extending beyond the meaning and purpose of the claims. The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.5 Diseases and Conditions that can be Treated with Anti-inflammatory Antibodies Anti-inflammatory antibodies may be used for treating a number of inflammatory diseases and conditions that are triggered by binding of natural IgG antibodies. For instance, the anti-inflammatory antibodies may be used to treat inflammatory diseases or conditions such as reperfusion injury, ischemia injury, stroke, autoimmune hemolytic anemia, idiopathic thrombocytopenic purpura, rheumatoid arthritis, celiac disease, hyper-IgG immunodeficiency, arteriosclerosis, coronary artery disease, sepsis, myocarditis, encephalitis, transplant rejection, hepatitis, thyroiditis (e.g., Hashimoto's thyroiditis, Graves disease), osteoporosis, polymyositis, dermatomyositis, Type I diabetes, gout, dermatitis, alopecia greata, systemic lupus erythematosus, lichen sclerosis, ulcerative colitis, diabetic retinopathy, pelvic inflammatory disease, periodontal disease, arthritis, juvenile chronic arthritis (e.g., chronic iridocyclitis), psoriasis, osteoporosis, nephropathy in diabetes mellitus, asthma, pelvic inflammatory disease, chronic inflammatory liver disease, chronic inflammatory lung disease, lung fibrosis, liver fibrosis, rheumatoid arthritis, chronic inflammatory liver disease, chronic inflammatory lung disease, lung fibrosis, liver fibrosis, Crohn's disease, ulcerative colitis, burn injury (or thermal injury), and other acute and chronic inflammatory diseases of the Central Nervous System (CNS; e.g., multiple sclerosis), gastrointestinal system, the skin and associated structures, the immune system, the hepato-biliary system, or any site in the body where pathology can occur with an inflammatory component.

Thus, provided herein are methods of inhibiting activation of an immune response to an ischemic antigen in a subject by administering to a subject an anti-inflammatory antibody described herein. In a further aspect, the invention features methods of treating an inflammatory disease or condition, such as e.g., ischemia-reperfusion injury, in a subject by administering to the subject a pharmaceutical composition comprising an anti-inflammatory antibody as disclosed herein.

An inflammatory condition such as reperfusion or ischemic injury may result following a naturally occurring episode, e.g., as a stroke or myocardial infarction. Reperfusion or ischemic injury may also occur during and/or following a surgical procedure. Exemplary surgical procedures that cause can cause injury include a vessel-corrective technique selected from the group consisting of angioplasty, stenting procedure, atherectomy, and bypass surgery. In an exemplary embodiment, reperfusion or ischemic injury occurs in a cardiovascular tissue, such as the heart.

In addition, diseases or conditions that are triggered by binding of natural IgG antibodies may be treated or prevented in a subject by removing from the subject or inactivating a natural or pathogenic IgG and/or B cells producing the pathogenic immunoglobulin (e.g., B-1 cells as described herein), thereby reducing the amount of the pathogenic immunoglobulin and/or B cells present in the subject.

The methods described herein may comprise removing from the subject or inactivating a pathogenic immunoglobulin, e.g., a pathogenic IgG as described herein, and/or B-cells producing the pathogenic IgG (e.g., B-1 cells as described herein), thereby reducing the amount of the pathogenic immunoglobulin and/or B cells present in the subject.

In one embodiment, the removing or inactivating step is performed ex vivo. The pathogenic immunoglobulins or B cells can be removed by hemoperfusion. Alternatively, the B cells can be removed using a B cell-specific antibody (e.g., an anti-B-1 antibody or an anti-CD5 antibody or anti-CD 11 G/CD 18). The pathogenic immunoglobulin, e.g., an IgG, can be removed by contacting blood from a subject with an immobilized antigen (e.g., an ischemia-specific antigen) or an immobilized anti-idiotypic antibody. The removing or inactivating step of the pathogenic immunoglobulin may be performed by administering an anti-idiotypic antibody to the subject. In another embodiment, the removing or inactivating step of the B cell is performed by administering to the subject a B cell targeting moiety (e.g., an antibody or an antigen) coupled to a toxin, e.g., ricin or diphteria toxin. The subject is a mammal, e.g., a rodent (e.g., a mouse) or a primate (e.g., a human). In a exemplary embodiment, the subject has sustained a reperfusion or ischemic injury following a naturally occurring episode, e.g., as a stroke, and the removing step is carried out within minutes, one to five hours, five to ten hours, ten to twenty hours, one to five days, following the naturally occurring episode. In another exemplary embodiment, the reperfusion or ischemic injury occurs in a cardiovascular tissue, e.g., the heart, and the reperfusion or ischemic injury is prevented and/or decreased by, removing from the subject, the pathogenic immunoglobulin, and/or the B cells, prior to, during, and/or following the surgical procedure. For example, the removing step can be carried out at least one to five hours, five to ten hours, ten to twenty hours, or one, two or three days prior to the surgical procedure. The removing step can also be continued for appropriate time intervals during and after the surgical procedure.

EXEMPLIFICATION

The invention, having been generally described, may be more readily understood by reference to the following examples, which are included merely for purposes of illustration of certain aspects and embodiments of the present invention, and are not intended to limit the invention in any way.

Example 1

Mechanism of Ischemia-Reperfusion Injury

This Example shows that mice deficient in the complement system were resistant to ischemia-reperfusion injury.

To examine the mechanism of ischemia-reperfusion injury, mice deficient in complement C3 were treated in the hindlimb model. The C3−/− mice were partially protected from injury based on an approximate 50% reduction in permeability index (see Weiser et al. (1996) *J. Exp. Med.* 1857-1864). Thus, complement C3 is essential for induction of full injury in this murine model.

The experiments in Weiser et al. did not identify how complement was activated. The serum complement system can be activated by at least three distinct pathways, classical, lectin or alternative. Knowing which pathway is involved, is important as it suggests a mechanism for injury. For example, the classical pathways is activated very efficiently by IgM and IgG isotypes of immunoglobulin or by the serum recognition protein C-reactive protein. Whereas, the lectin pathway is activated following recognition of specific carbohydrates such as mannan by mannan binding lectin (MBL) (Epstein et al., (1996) *Immunol* 8, 29-35). In both pathways, complement C4 is required in forming an enzyme complex with C2 that catalyzes cleavage of the central component C3. By contrast, the alternative pathway activates spontaneously leading to conversion of C3 to its active form (C3b) and attachment to foreign- or self-tissues. The pathway is tightly regulated as all host cells express inhibitors of amplification of the complement pathway by inactivating, or displacing the C3 convertase (Muller-Eberhard, H. J., (1988) *Ann. Rev. Biochem.* 57, 321-347). One approach for determining the pathway involved is use of mice deficient in C4, i.e., cannot form C3 convertase via classical or lectin pathways. Comparison of mice deficient in either C3 or C4 with wild type (WT) controls in the hindlimb model, revealed that C4 was also required for induction of full injury (Weiser et al. supra). This finding was important as it suggested that antibody or MBL might be involved.

Example 2

Natural IgM Mediates Ischemia Reperfusion (I/R) Injury

This Example shows that mice deficient in immunoglobulin were resistant to ischemia-reperfusion injury.

To determine if antibody was involved in mediating I/R injury, mice totally deficient in immunoglobulin, RAG2−/− (recombinase activating gene-2 deficient) were characterized along with the complement deficient animals in the intestinal model. Significantly, the RAG-2−/− mice were protected to a similar level as observed in the complement deficient animals (Weiser et al. supra). Since the RAG2−/− animals are also missing mature lymphocytes, it was important to determine that the pathogenic effect was antibody dependent (Shinkai et al. (1992) *Cell* 68, 855-867). To confirm that injury was mediated by serum antibody, the deficient animals were reconstituted with either normal mouse sera (Weiser et al. supra) or purified IgM (Williams et al. (1999) *J. Appl. Physiol* 86; 938-42). In both cases, the reconstituted RAG-2−/− mice were no longer protected and injury was restored. In the latter experiments, a model of intestinal injury was used as in this model, injury is thought to be mediated primarily by complement.

The interpretation of these results is that during the period of ischemia, neoantigens are either expressed or exposed on the endothelial cell surface. Circulating IgMs appear to recognize the new determinant, bind and activate classical pathway of complement. While the nature of the antigen is not known, IgM rather than IgG seems to be primarily responsible for activation of complement as reconstitution of deficient mice with pooled IgG did not significantly restore injury in the mice. An alternative hypothesis is that there is another initial event such as the MBL pathway that recognizes the altered endothelial surface, induces low level complement activation which in turn exposes new antigenic sites and the pathway is amplified by binding of IgM.

Example 3

Pathogenic IgM is a Product of B-1 Cells

Since a major fraction of circulating IgM is thought to represent natural antibody, i.e. product of rearranged germ-line genes, it is possible that mice bearing deficiencies in the B-1 fraction of lymphocytes might also be protected. B-1 cells have a distinct phenotype from more conventional B-2 cells in that they express low levels of IgD and CD23 and a major fraction express the cell surface protein CD5 (Hardy et al., (1994) *Immunol. Rev.:* 137, 91; Kantor et al. (1993) *Annu. Rev. Immunol.* 11, 501-538, 1993. B-1 cells are also distinguished by reduced circulation in mice, limited frequency in the peripheral lymph nodes and spleen and are primarily localized within the peritoneal cavity. To examine a role for B-1 cells as a source of pathogenic IgM, antibody-deficient mice (RAG-2−/−) were reconstituted with $5 \times 10^5$ peritoneal B-1 cells and rested approximately 30 days before treatment. Circulating IgM levels reach a near normal range within a month following adoptive transfer. Characterization of the B-1 cell reconstituted mice in the intestinal ischemia model confirmed that B-1 cells were a major source of pathogenic IgM (see Williams et al. (1999) supra). This was an important observation because the repertoire of B-1 cell natural antibody is considerably more limited than would be expected for conventional B-2 cells. Therefore, it is possible that the pathogenic antibody represents a product of the germline.

Example 4

Cr2−/− Mice are Protected from Ischemia Reperfusion Injury

The initial characterization of Cr2−/− knockout mice revealed an approximate 50% reduction in the frequency of B-1a or CD5+B-1 cells (Ahearn et al. (1996) *Immunity* 4: 251-262). Although characterization of another strain of Cr2-deficient mice did not identify a similar reduction (Molina et al. (1996) *Proc. Natl. Acad. Sci. USA* 93, 3357-3361). Whether the difference in frequency of CD5+cells was due to variation in strain background or environmental differences is not known. Despite the reduced frequency of B-1a cells in the Cr2−/− mice, circulating levels of IgM were within the normal range. These findings suggested that the repertoire of IgM might be different in the Cr2-deficient animals. To test this hypothesis, mice in the intestinal I/R model were characterized. Surprisingly, the Cr2−/− mice were equally protected as the complete-antibody deficient mice. Comparison of survival over a five-day period following treatment in the intestinal model demonstrated a significant increase in mortality of the WT compared to Cr2-deficient animals. Consistent with an increased mortality, a dramatic reduction in injury was observed in tissue sections harvested from treated WT or Cr2−/− deficient mice.

Extensive injury to the mucosal layer of the intestine was observed in WT mice or Cr2−/− mice reconstituted with pooled IgM or B-1 cells. By contrast, tissue sections isolated from treated Cr2−/− mice were similar to that of sham controls. Thus, despite normal circulating levels of IgM, the Cr2-deficient mice were protected from injury. These results not only confirm the importance of B-1 cells as a source of pathogenic antibody but suggest that the complement system is somehow involved in formation or maintenance of the repertoire of natural antibody. For example, complement may be involved in positive selection of B-1 cells.

Example 5

Identification of Pathogenic IgMs

This Example describes the generation of a specific hybridoma clone from normal B-1 cells and the identification of one clone that produces a pathogenic IgM. The pathogenic IgM was shown to restore injury in vivo to antibody deficient mice.

Studies in mice bearing a deficiency in complement receptors CD21/CD35, revealed that the mice were missing the pathogenic antibody. This finding was unexpected because they have a normal level of IgM in their blood. These findings led to the hypothesis that a special population of B cells termed B-1 cells are responsible for secreting the pathogenic IgM. For example, engraftment of the receptor deficient mice (Cr2−/−) with B-1 cells from normal mice restored injury, confirming the importance of B-I cells. To identify the specific antibody or antibodies responsible for injury, a panel of hybridoma clones were constructed from an enriched pool of peritoneal B-1 cells harvested from normal mice. The general approach for preparing hybridomas from enriched fraction of peritoneal cells includes harvesting peritoneal cells from mice treated 7 days earlier with IL-10 and subsequently enriched for CD23 negative B cells by negative selection with magnetic beads. Enriched B cells are analyzed by FACS following staining with IgM, Mac-1 and CD23 specific Mab. The enriched population is further activated by culturing with LPS for 24 hours. Activated cells are hybridized with fusion partner myeloma cells in the presence of PEG and grown in HAT-selective medium. Hybridomas are screened for IgM secreting clones by ELISA, and positive wells are expanded for purification of IgM.

Twenty-two IgM-secreting hybridoma clones were analyzed by pooling an equal amount of IgM product from each of the clones. Treatment of antibody-deficient mice with the pooled IgM restored injury similar to that seen with pooled IgM from serum. This finding confirmed that the pathogenic IgM was among the twenty-two hybridomas produced. By dividing the pools into two fractions, i.e., 1-11 and 12-22, and treatment mice with the two fractions, the pathogenic antibody was found to fractionate with the pool that included clone #22. Finally, mice were reconstituted with either clone 17 or 22. Clone 22 restored injury whereas the other clones did not.

Example 6

Complement Involvement in B-1 Cell Selection

Two different models have been proposed to explain the development of B-1 cells. The lineage hypothesis proposes that B-1 cells develop in early fetal life as a distinct population (Kantor et al. (1993) supra). Alternatively, B-1 cells develop from the same progenitors as conventional B cells but depending on their environment, i.e., encounter with antigen, they develop into B-1 or retain the B-2 cell phenotype (Wortis, H. H. (1992) Int. Rev. Immunol. 8, 235; Clarke, J. (1998) *Exp. Med.* 187, 1325-1334). Irrespective of their origin, it is known that B-1 cells are not replenished from adult bone marrow at the same frequency as B-2 cells and that their phenotype is more similar to that of early fetal liver B cells or neonatal bone marrow (BM) cells. Consistent with an early origin, their repertoire tends to be biased towards expression of more proximal $V_H$ genes and N-nucleotide addition is limited (Gu et al. (1990) *EMBO J.* 9, 2133; Feeney, J. (1990) *Exp. Med.* 172, 1377). It seems reasonable that given the reduced replenishment by adult BM stem cells, B-1 cells are self-renewed and that antigen stimulation might be important in their renewal, expansion or even initial selection (Hayakawa et al., (1986) *Eur. J. Immunol.* 16, 1313). Indeed inherent to the conventional model, B-1 cells must be antigen selected.

Evidence in support of a B-cell receptor (BCR) signaling requirement for positive selection of B-1 cells comes from mice bearing mutations that alter BCR signaling. For example, impairment of BCR signaling through CD 19, vav, or Btk dramatically affects development of B-1 cells. By contrast, loss of negative selection such as in CD22- or SHIP-1 deficient mice can lead to an increase in B-1 cell frequency (O'Keefe et al. (1996) *Science* 274, 798-801; Shultz et al. (1993) *Cell* 73, 1445). Recent, elegant studies with mice bearing two distinct Ig transgenes, $V_H12$ (B-1 cell phenotype) or $V_HB1$-8 (B-2 cell phenotype) support the view that B-1 cells are positively selected by self-antigens. For example, B cells expressing $V_H12$ either alone or together with B1-8 developed a B-1 cell phenotype. Whereas, few if any B cells were identified that expressed the B1-8 transgene only. Thus, these results suggested that encounter of transgenic B cells with self-PtC resulted in expansion of those expressing $V_H$ 12. Selection of B-1 cells was recently reported by Hardy et al. (1994) *Immunol. Rev.* 137, 91). In their model, B cells expressing an immunoglobulin transgene specific for Thy 1.1 were selected and expanded in mice expressing the cognate antigen. By contrast, transgene+B-1 cells were not found in mice that expressed the alternative allotype Thy 1.2.

Where does complement fit into B-1 cell development? The overall reduction in B-1a cell frequency and the more specific loss of B-1 cells expressing IgM involved in I/R injury suggests a role for CD21/CD35 in either positive selection or maintenance of B-1a cells. One possible role for complement is that it enhances BCR signaling on encounter with cognate antigen. Biochemical studies and analysis of CD21/CD35 deficient mice demonstrate the importance of co-receptor signaling in activation and survival of conventional B cells (Carroll, M. C., (1998) *Ann. Rev. Immunol.* 16, 545-568; Fearon et al. (1995) *Annu. Rev. Immunol.* 13, 127-149). It is very likely that B-1 cells likewise utilize co-receptor signaling to enhance the BCR signal. For example, bacteria express typical B-1 cell antigens such as phosphoryl choline and it is not unreasonable that coating of bacteria with complement ligand C3d would enhance crosslinking of the co-receptor with the BCR and enhance overall signaling. Thus, antigens expressed at lower concentrations might require complement enhancement in order for the cognate B-cell to recognize it and expand or be positively selected. Another role for complement receptors is in localizing antigen on follicular dendritic cells (FDC) within the lymphoid compartment. However, since the major population of B-1 cells occupy the peritoneal tissues it is not clear if they would encounter FDC within lymphoid structures. The actual site or sites in which B-1 cells undergo positive selection are not known. It is possible that they must encounter cognate antigen in early fetal development or in neonatal BM. If this is the case, it might be expected that complement receptors on stromal cells within these compartments bind antigen for presentation to B cells. It is possible that complement receptors could participate in both stages of development. First, they might enhance antigens signaling in initial positive selection. Secondly, as selected B-1 cells are replenished at peripheral sites, complement receptors might again be involved in enhancement of BCR signaling.

A proposed role for complement and complement receptors in positive selection of peritoneal B-1 lymphocytes includes the interaction of complement-ligand coated antigens (self- and non-self), resulting in co-ligation of the CD21/CD19 co-receptor and BCR on the cell surface, in turn, leading to enhanced signaling and positive selection.

Example 7

12A6 and 21G6 Hybridomas

A panel of mouse hybridomas were prepared to identify the N2 region of non-muscle myosin II heavy chain. Thus, mice were immunized with the N2 peptide (Ac-LMKNMDPLNDNV (SEQ ID NO: 33)) coupled to a carrier protein (KLH). This region (N2) is highly conserved and identical in mouse and man. Two of the hybridomas were selected for further characterization and shown to bind the N2 peptide both in vitro and in vivo. Importantly, pretreatment of mice with 100 ugs of a Fab'2 fragment (removal of the Fc piece) of either hybridoma blocks ischemia reperfusion injury in the murine myocardial infarction model. 12A6 is a IgG2b isotype. Its VH most closely matches the germ line gene 3609.11.169 sequence paired with DH: DSP2/DFL16.1 and its light chain is a V kappa 8-27 with JK1. 21G6 is an IgG1 isotype with its VH matching J558.35; DH: DSP2.6/DSP2.4/DSP2.3 and JH: JH3. Its light chain is V kappa hf24 and JK4.

Murine anti-N2 mAb inhibits inflammation following myocardial infarction. B6 mice were subjected to 1 h LAD occlusion followed by 24 h reperfusion. Prior to occlusion (15 min), either saline or 150 µg of anti-N2 F(ab')$_2$ antibody (21G6) was injected i.v. into the mice. Following reperfusion, both serum troponin-I levels (A) and mouse IgM deposition (B) were analyzed and statistical significance for each was evaluated by Student's t test (FIG. 3).

Figure 4:
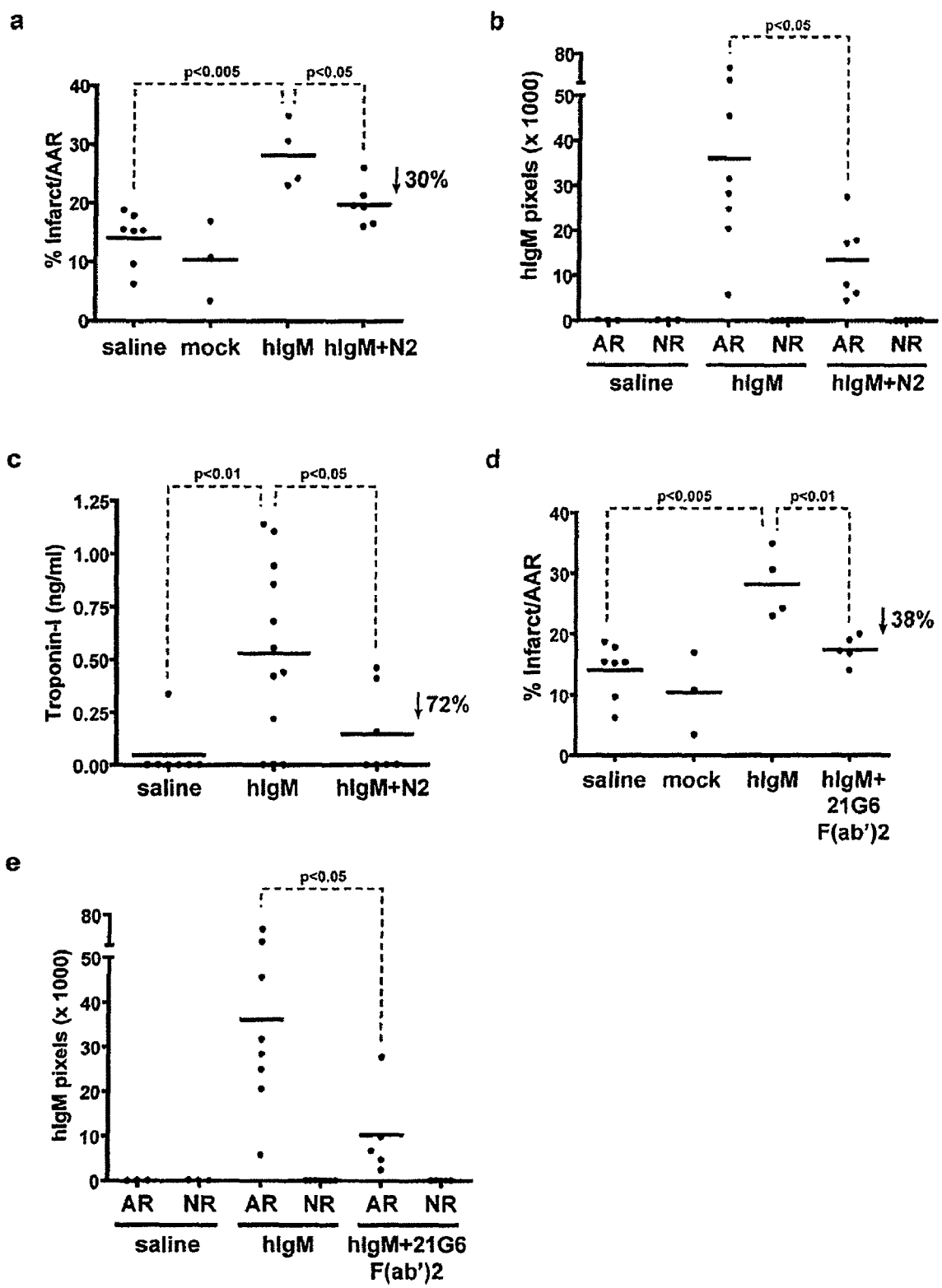
FIG. 4 shows that N2 peptide and anti-N2 mAb (anti-N2 F(ab')$_2$ antibody (21G6)) block human IgM-mediated injury.

N2 peptide and anti-N2 mAb block human IgM-mediated injury. FIG. 4 shows (A) RAG-1-/- mice were subjected to 1 h LAD occlusion followed by 24 h reperfusion. Prior to occlusion (15 min), 400 µg of pooled individual hIgM from 10 donors was injected i.v. into the mice with either saline or 200 µg of N2 peptide. Myocardial sections were stained with Evans blue and TTC. Myocardial infarct size is expressed as a percentage infarct of the area at risk (AAR) of the left ventricle. (B and C) RAG-1-/- mice were treated as in (A) and analyzed for hIgM deposition (B) or serum troponin-I levels (C). (D) RAG-1-/- mice were subjected to 1 h LAD occlusion and 24 h reperfusion. Prior to occlusion (15 min), 400 µg hIgM was injected i.v. into the mice with either saline or 150 µg of anti-N2 F(ab')$_2$ antibody (21G6) and myocardial sections were analyzed as in (A). (E) RAG-1-/- mice were treated as in (D) and analyzed for hIgM deposition. In all panels, statistical significance was evaluated by Student's t test.

Example 8

12A6 Hybridoma Antibody Binds to the N2 Self-peptide In Vivo

Figure 5:
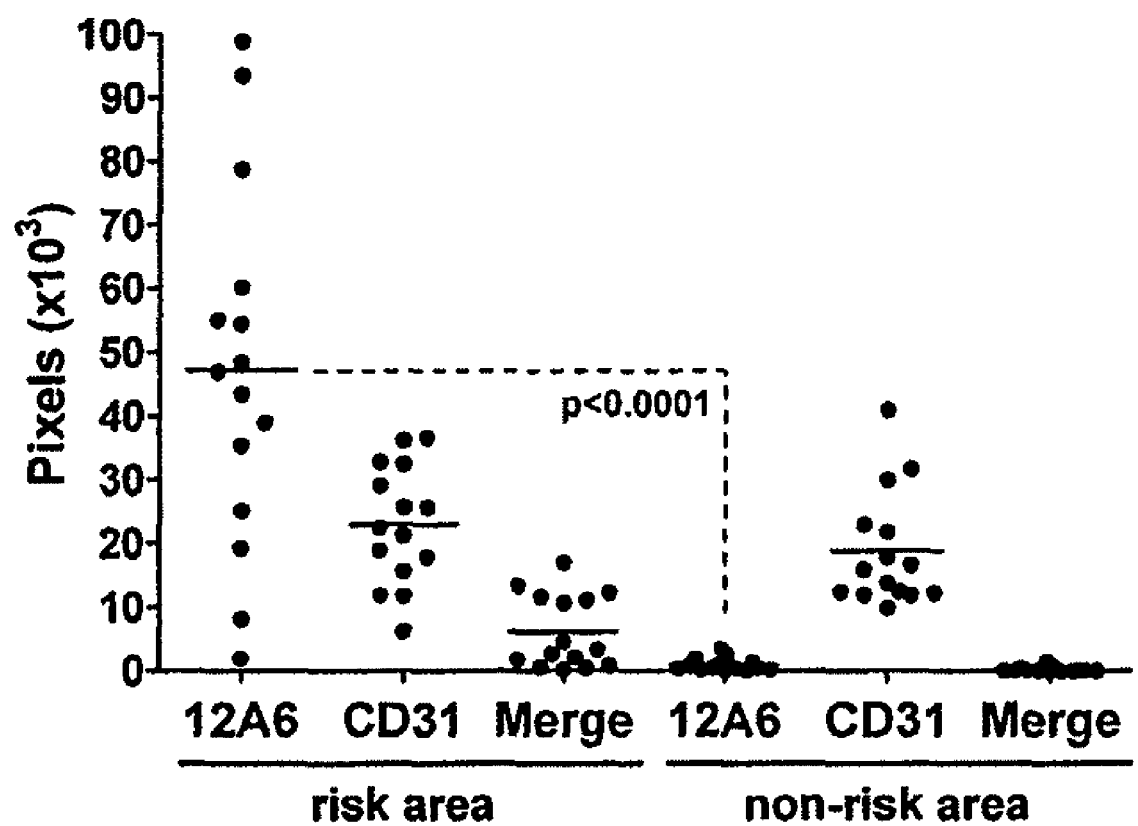
FIG. 5 shows binding of the 12A6 hybridoma antibody to antigen released in small vessels in the heart after reperfusion

Specificity of the anti-N2 antibody. B6 mice were injected i.v. with fluorescently-labeled anti-N2 antibody (12A6) and anti-CD31 antibody prior to 60 min LAD occlusion and 30 min reperfusion. Following treatment, hearts were collected, fixed, and analyzed by confocal microscopy. The area at risk (left ventricle) was compared with the non-risk area (right ventricle). Quantification of the individual antibody staining as well as the merged images both in the area at risk and non-risk area is shown in FIG. 5.

Figure 6:
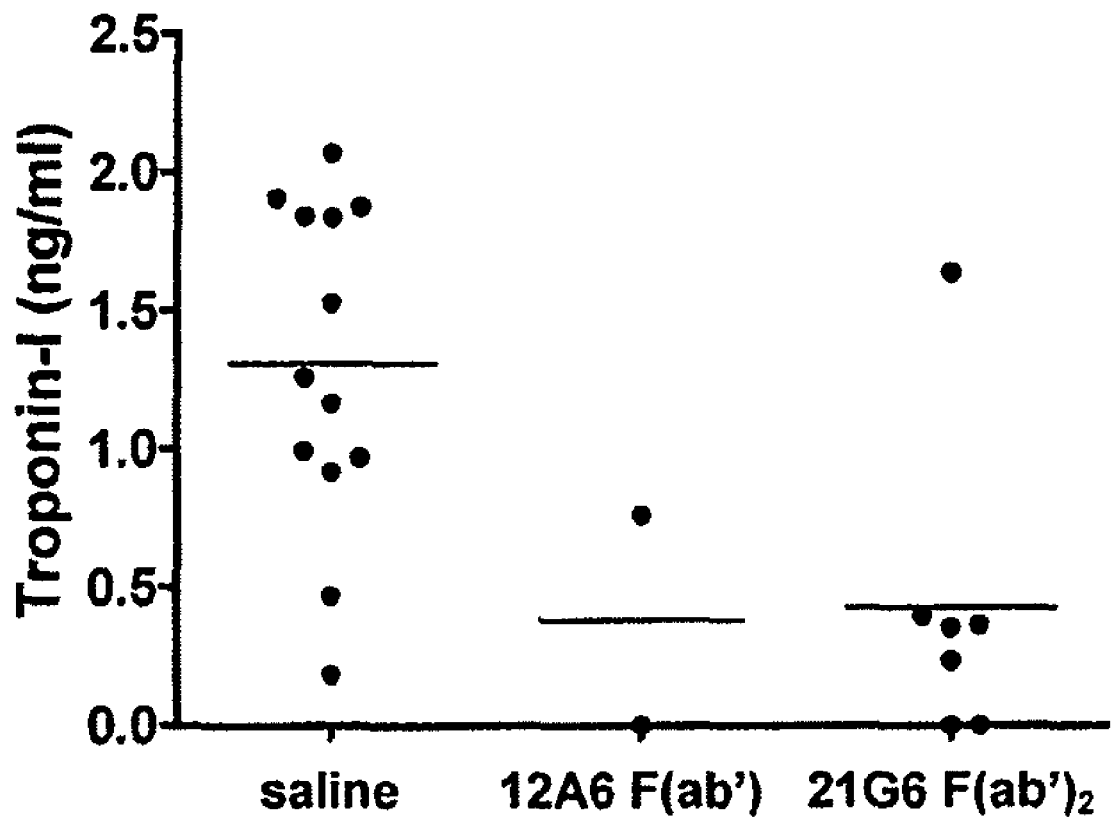
FIG. 6 shows the results of a blocking experiment with an Fab'2 fragment of 12A6 as compared to 21G6.

Effect of serum troponin-I levels in B6 mice treated with anti-N2 antibodies. Saline, 12A6 F(ab')2 (150 µg), or 21G6 F(ab')2 (150 µg) was injected i.v. into B6 mice prior to 1 h LAD occlusion and 24 h of reperfusion. Serum troponin-I levels were measured after 24 h reperfusion. Results are shown in FIG. 6.

Incorporation By Reference

All publications, patents, and patent applications mentioned herein are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequence which reference an accession number correlating to an entry in a public database, such as those maintained by The Institute for Genomic Research (TIGR) on the world wide web with the extension tigr.org and or the National Center for Biotechnology Information (NCBI) on the world wide web with the extension ncbi.nlm.nih.gov.

Equivalents

Those skilled in the art will recognize, or be able to ascertain using no more than routine experimentation, many equivalents to the specific embodiments of the invention described herein. Such equivalents are intended to be encompassed by the following claims.

---

The invention claimed is:

1. An isolated anti-inflammatory antibody which specifically binds to the N2 self-peptide, wherein the antibody comprises:
   a) an amino acid sequence comprising a variable heavy (VH) complementarity determining region (CDR) 1 selected from the group consisting of SEQ ID NO: 4 and 16;
   b) an amino acid sequence comprising a VH CDR2 selected from the group consisting of SEQ ID NO: 6 and 18;
   c) an amino acid sequence comprising a VH CDR3 selected from the group consisting of SEQ ID NO: 26 and 30;
   d) an amino acid sequence comprising a variable light (VL) CDR1 selected from the group consisting of SEQ ID NO: 10 and 22;
   e) an amino acid sequence comprising a VL CDR2 selected from the group consisting of SEQ ID NO: 12 and 24; and
   f) an amino acid sequence comprising a VL CDR3 selected from the group consisting of SEQ ID NO: 28 and 32.

2. The isolated anti-inflammatory antibody of claim 1, wherein the antibody is a humanized antibody.

3. The isolated anti-inflammatory antibody of claim 1, wherein the antibody is an Fab fragment, an F(ab')$_2$ fragment, or a scFv.

4. The isolated anti-inflammatory antibody of claim 1, wherein the antibody is an IgG antibody.

5. A pharmaceutical composition comprising the anti-inflammatory antibody of claim 1 and a pharmaceutically acceptable carrier.

6. The isolated anti-inflammatory antibody of claim 1, which is produced by a hybridoma having ATCC deposit number selected from the group consisting of PTA-9392 and PTA-9393.

7. The isolated anti-inflammatory antibody of claim 1, wherein the antibody comprises:
   a) the variable heavy (VH) complementarity determining region (CDR) 1 shown as SEQ ID NO: 4;
   b) the VH CDR2 shown as SEQ ID NO: 6;
   c) the VH CDR3 shown as SEQ ID NO: 26;
   d) the variable light (VL) CDR1 shown as SEQ ID NO: 10;
   e) the VL CDR2 shown as SEQ ID NO: 12; and
   f) the VL CDR3 shown as SEQ ID NO: 28.

8. The isolated anti-inflammatory antibody of claim 1, wherein the antibody comprises:
   a) the variable heavy (VH) complementarity determining region (CDR) 1 shown as SEQ ID NO: 16;
   b) the VH CDR2 shown as SEQ ID NO: 18;
   c) the VH CDR3 shown as SEQ ID NO: 30;
   d) the variable light (VL) CDR1 shown as SEQ ID NO: 22;
   e) the VL CDR2 shown as SEQ ID NO: 24; and
   f) the VL CDR3 shown as SEQ ID NO: 32.

* * * * *

SEQUENCE LISTING

```
<160> NUMBER OF SEQ ID NOS: 35

<210> SEQ ID NO 1
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 1 cag gtt act ctg aaa gag tct ggc cct ggg ata ttg cag ccc tcc cag      48
Gln Val Thr Leu Lys Glu Ser Gly Pro Gly Ile Leu Gln Pro Ser Gln
1               5                   10                  15 acc ctc agt ctg act tgt tct ttc tct gga ttt tca ctg agc act ttt      96
Thr Leu Ser Leu Thr Cys Ser Phe Ser Gly Phe Ser Leu Ser Thr Phe
            20                  25                  30 ggt ata gga gta ggc tgg att cgt cag cct tca ggg aag ggt ctg gag     144
Gly Ile Gly Val Gly Trp Ile Arg Gln Pro Ser Gly Lys Gly Leu Glu
        35                  40                  45 tgg ctg gca cac att tgg tgg aat gat aat aac tac tat aac aca tcc     192
Trp Leu Ala His Ile Trp Trp Asn Asp Asn Asn Tyr Tyr Asn Thr Ser
    50                  55                  60 ctg aag agc cgg ctc aca atc tcc aag gat acc tcc aac aac cag gta     240
Leu Lys Ser Arg Leu Thr Ile Ser Lys Asp Thr Ser Asn Asn Gln Val
65                  70                  75                  80 ttc ctc aag atc gcc agt gtg gac act gca gat act gcc aca tac tac     288
Phe Leu Lys Ile Ala Ser Val Asp Thr Ala Asp Thr Ala Thr Tyr Tyr
                85                  90                  95 tgt gct cga gta gga ggg att aac ttt tct atg gac tac tgg ggt caa     336
Cys Ala Arg Val Gly Gly Ile Asn Phe Ser Met Asp Tyr Trp Gly Gln
            100                 105                 110 gga acc tca gtc acc gtc tcc tca                                      360
Gly Thr Ser Val Thr Val Ser Ser
        115                 120

<210> SEQ ID NO 2
<211> LENGTH: 120
<212> TYPE: PRT
<213> ORGANISM: Mus sp.

<400> SEQUENCE: 2

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Asn Tyr Tyr Asn Thr Ser
    50                  55                  60

Leu Lys Ser Arg Leu Thr Ile Ser Lys Asp Thr Ser Asn Asn Gln Val
```

```
                65                  70                  75                  80
            Phe Leu Lys Ile Ala Ser Val Asp Thr Ala Asp Thr Ala Thr Tyr Tyr
                            85                  90                  95
            Cys Ala Arg Val Gly Gly Ile Asn Phe Ser Met Asp Tyr Trp Gly Gln
                        100                 105                 110
            Gly Thr Ser Val Thr Val Ser Ser
                    115                 120

<210> SEQ ID NO 3
<211> LENGTH: 21
<212> TYPE: DNA
<213> ORGANISM: Mus sp.
<220> FEATURE:
<221> NAME/KEY: CDS
<222> LOCATION: (1)..(21)

<400> SEQUENCE: 3 act ttt ggt ata gga gta ggc                                              21
Thr Phe Gly Ile Gly Val Gly
 1               5

<210> SEQ ID NO 4
<211> LENGTH: 7
<212> TYPE: PRT
<213> ORGANISM: Mus sp.

<400> SEQUENCE: 4

Thr Phe Gly Ile Gly Val Gly
 1               5

<210> SEQ ID NO 5
<211> LENGTH: 48
<212> TYPE: DNA
<213> ORGANISM: Mus sp.
<220> FEATURE:
<221> NAME/KEY: CDS
<222> LOCATION: (1)..(48)

<400> SEQUENCE: 5 cac att tgg tgg aat gat aat aac tac tat aac aca tcc ctg aag agc         48
His Ile Trp Trp Asn Asp Asn Asn Tyr Tyr Asn Thr Ser Leu Lys Ser
 1               5                  10                  15

<210> SEQ ID NO 6
<211> LENGTH: 16
<212> TYPE: PRT
<213> ORGANISM: Mus sp.

<400> SEQUENCE: 6

His Ile Trp Trp Asn Asp Asn Asn Tyr Tyr Asn Thr Ser Leu Lys Ser
 1               5                  10                  15

<210> SEQ ID NO 7
<211> LENGTH: 339
<212> TYPE: DNA
<213> ORGANISM: Mus sp.
<220> FEATURE:
<221> NAME/KEY: CDS
<222> LOCATION: (1)..(339)

<400> SEQUENCE: 7 gat att gtg atg acc cag tct gca tca tct ctg gct gtg tct gca gga         48
Asp Ile Val Met Thr Gln Ser Ala Ser Ser Leu Ala Val Ser Ala Gly
 1               5                  10                  15 gaa aag gtc act atg aac tgt aag tcc agt caa agt gtt tta tac agt         96
Glu Lys Val Thr Met Asn Cys Lys Ser Ser Gln Ser Val Leu Tyr Ser
```

```
                    20                  25                  30
tca aat cag aag aac tac ttg gcc tgg tac cag cag aaa cca ggg cag        144
Ser Asn Gln Lys Asn Tyr Leu Ala Trp Tyr Gln Gln Lys Pro Gly Gln
         35                  40                  45 tct cct aaa ctg ctg atc tac tgg gca tcc act agg gaa tct ggt gtc        192
Ser Pro Lys Leu Leu Ile Tyr Trp Ala Ser Thr Arg Glu Ser Gly Val
 50                  55                  60 cct gat cgc ttc aca ggc agt gga tct ggg aca gat ttt act ctt acc        240
Pro Asp Arg Phe Thr Gly Ser Gly Ser Gly Thr Asp Phe Thr Leu Thr
 65                  70                  75                  80 atc agc agt gta caa gct gaa gac ctg gca gtt tat tac tgt cat caa        288
Ile Ser Ser Val Gln Ala Glu Asp Leu Ala Val Tyr Tyr Cys His Gln
                 85                  90                  95 tac ctc tcc tcg tgg acg ttc ggt gga ggc acc aag ctg gaa atc aaa        336
Tyr Leu Ser Ser Trp Thr Phe Gly Gly Gly Thr Lys Leu Glu Ile Lys
            100                 105                 110 cgg                                                                    339
Arg

<210> SEQ ID NO 8
<211> LENGTH: 113
<212> TYPE: PRT
<213> ORGANISM: Mus sp.

<400> SEQUENCE: 8

Asp Ile Val Met Thr Gln Ser Ala Ser Ser Leu Ala Val Ser Ala Gly
 1               5                  10                  15

Glu Lys Val Thr Met Asn Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys His Gln
                 85                  90                  95

Tyr Leu Ser Ser Trp Thr Phe Gly Gly Gly Thr Lys Leu Glu Ile Lys
            100                 105                 110

Arg

<210> SEQ ID NO 9
<211> LENGTH: 51
<212> TYPE: DNA
<213> ORGANISM: Mus sp.
<220> FEATURE:
<221> NAME/KEY: CDS
<222> LOCATION: (1)..(51)

<400> SEQUENCE: 9 aag tcc agt caa agt gtt tta tac agt tca aat cag aag aac tac ttg        48
Lys Ser Ser Gln Ser Val Leu Tyr Ser Ser Asn Gln Lys Asn Tyr Leu
 1               5                  10                  15 gcc                                                                    51
Ala

<210> SEQ ID NO 10
<211> LENGTH: 17
<212> TYPE: PRT
<213> ORGANISM: Mus sp.
```

-continued

```
<400> SEQUENCE: 10

Lys Ser Ser Gln Ser Val Leu Tyr Ser Ser Asn Gln Lys Asn Tyr Leu
1               5                   10                  15

Ala

<210> SEQ ID NO 11
<211> LENGTH: 21
<212> TYPE: DNA
<213> ORGANISM: Mus sp.
<220> FEATURE:
<221> NAME/KEY: CDS
<222> LOCATION: (1)..(21)

<400> SEQUENCE: 11 tgg gca tcc act agg gaa tct                                         21
Trp Ala Ser Thr Arg Glu Ser
1               5

<210> SEQ ID NO 12
<211> LENGTH: 7
<212> TYPE: PRT
<213> ORGANISM: Mus sp.

<400> SEQUENCE: 12

Trp Ala Ser Thr Arg Glu Ser
1               5

<210> SEQ ID NO 13
<211> LENGTH: 357
<212> TYPE: DNA
<213> ORGANISM: Mus sp.
<220> FEATURE:
<221> NAME/KEY: CDS
<222> LOCATION: (1)..(357)

<400> SEQUENCE: 13 cag gtc cag ctg cag gag tct ggg gct gaa ctg gtg aag cct ggg gct    48
Gln Val Gln Leu Gln Glu Ser Gly Ala Glu Leu Val Lys Pro Gly Ala
1               5                   10                  15 tca gtg aag ttg tcc tgc aag gct tct ggc tac acc ttc acc agc tac    96
Ser Val Lys Leu Ser Cys Lys Ala Ser Gly Tyr Thr Phe Thr Ser Tyr
            20                  25                  30 tat atg tac tgg gtg aag cag agg cct gga caa ggc ctt gag tgg att    144
Tyr Met Tyr Trp Val Lys Gln Arg Pro Gly Gln Gly Leu Glu Trp Ile
        35                  40                  45 ggg ggg att aat cct agc aat ggt ggt act aac ttc aat gag aag ttc    192
Gly Gly Ile Asn Pro Ser Asn Gly Gly Thr Asn Phe Asn Glu Lys Phe
    50                  55                  60 aag agc aag gcc aca ctg act gta gac aaa tcc tcc agc aca gcc tac    240
Lys Ser Lys Ala Thr Leu Thr Val Asp Lys Ser Ser Ser Thr Ala Tyr
65                  70                  75                  80 atg caa ctc agc agc ctg aca tct gag gac tct gcg gtc tat tac tgt    288
Met Gln Leu Ser Ser Leu Thr Ser Glu Asp Ser Ala Val Tyr Tyr Cys
                85                  90                  95 aca aga tgg ggt tac gac agg gag tgg ttt gct tac tgg ggc caa ggg    336
Thr Arg Trp Gly Tyr Asp Arg Glu Trp Phe Ala Tyr Trp Gly Gln Gly
            100                 105                 110 act ctg gtc act gtc tct gca                                         357
Thr Leu Val Thr Val Ser Ala
        115

<210> SEQ ID NO 14
<211> LENGTH: 119
<212> TYPE: PRT
```

<213> ORGANISM: Mus sp.

<400> SEQUENCE: 14

| Gln | Val | Gln | Leu | Gln | Glu | Ser | Gly | Ala | Glu | Leu | Val | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Leu | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Tyr | Met | Tyr | Trp | Val | Lys | Gln | Arg | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Gly | Ile | Asn | Pro | Ser | Asn | Gly | Gly | Thr | Asn | Phe | Asn | Glu | Lys | Phe |
|---|---|---|---|---|---|---|---|---|---|---|---|---|---|---|---|
| | 50 | | | | | 55 | | | | | 60 | | | | |

| Lys | Ser | Lys | Ala | Thr | Leu | Thr | Val | Asp | Lys | Ser | Ser | Ser | Thr | Ala | Tyr |
|---|---|---|---|---|---|---|---|---|---|---|---|---|---|---|---|
| 65 | | | | | 70 | | | | | 75 | | | | | 80 |

| Met | Gln | Leu | Ser | Ser | Leu | Thr | Ser | Glu | Asp | Ser | Ala | Val | Tyr | Tyr | Cys |
|---|---|---|---|---|---|---|---|---|---|---|---|---|---|---|---|
| | | | | 85 | | | | | 90 | | | | | 95 | |

| Thr | Arg | Trp | Gly | Tyr | Asp | Arg | Glu | Trp | Phe | Ala | Tyr | Trp | Gly | Gln | Gly |
|---|---|---|---|---|---|---|---|---|---|---|---|---|---|---|---|
| | | | 100 | | | | | 105 | | | | | 110 | | |

| Thr | Leu | Val | Thr | Val | Ser | Ala |
|---|---|---|---|---|---|---|
| | | | 115 | | | |

<210> SEQ ID NO 15
<211> LENGTH: 15
<212> TYPE: DNA
<213> ORGANISM: Mus sp.
<220> FEATURE:
<221> NAME/KEY: CDS
<222> LOCATION: (1)..(15)

<400> SEQUENCE: 15

| agc | tac | tat | atg | tac | | | | | | | | | | | | 15 |
|---|---|---|---|---|---|---|---|---|---|---|---|---|---|---|---|---|
| Ser | Tyr | Tyr | Met | Tyr | | | | | | | | | | | | |
| 1 | | | | 5 | | | | | | | | | | | | |

<210> SEQ ID NO 16
<211> LENGTH: 5
<212> TYPE: PRT
<213> ORGANISM: Mus sp.

<400> SEQUENCE: 16

| Ser | Tyr | Tyr | Met | Tyr |
|---|---|---|---|---|
| 1 | | | | 5 |

<210> SEQ ID NO 17
<211> LENGTH: 51
<212> TYPE: DNA
<213> ORGANISM: Mus sp.
<220> FEATURE:
<221> NAME/KEY: CDS
<222> LOCATION: (1)..(51)

<400> SEQUENCE: 17

| ggg | att | aat | cct | agc | aat | ggt | ggt | act | aac | ttc | aat | gag | aag | ttc | aag | 48 |
|---|---|---|---|---|---|---|---|---|---|---|---|---|---|---|---|---|
| Gly | Ile | Asn | Pro | Ser | Asn | Gly | Gly | Thr | Asn | Phe | Asn | Glu | Lys | Phe | Lys | |
| 1 | | | | 5 | | | | | 10 | | | | | 15 | | |

| agc | 51 |
|---|---|
| Ser | |

<210> SEQ ID NO 18
<211> LENGTH: 17
<212> TYPE: PRT
<213> ORGANISM: Mus sp.

<400> SEQUENCE: 18

```
Gly Ile Asn Pro Ser Asn Gly Gly Thr Asn Phe Asn Glu Lys Phe Lys
1               5                   10                  15

Ser
```

<210> SEQ ID NO 19
<211> LENGTH: 339
<212> TYPE: DNA
<213> ORGANISM: Mus sp.
<220> FEATURE:
<221> NAME/KEY: CDS
<222> LOCATION: (1)..(339)

<400> SEQUENCE: 19

```
gat att gtg atg act cag gct gca ccc tct gta cct gtc act cct gga     48
Asp Ile Val Met Thr Gln Ala Ala Pro Ser Val Pro Val Thr Pro Gly
1               5                   10                  15 gag tca gta tcc atc tcc tgc agg tct agt aag agt ctc ctg cat agt     96
Glu Ser Val Ser Ile Ser Cys Arg Ser Ser Lys Ser Leu Leu His Ser
                20                  25                  30 aat ggc aac act tac ttg tat tgg ttc ctg cag agg cca ggc cag tct    144
Asn Gly Asn Thr Tyr Leu Tyr Trp Phe Leu Gln Arg Pro Gly Gln Ser
            35                  40                  45 cct cag gtc ctg ata tat cgg atg tcc aac ctt gcc tca gga gtc cca    192
Pro Gln Val Leu Ile Tyr Arg Met Ser Asn Leu Ala Ser Gly Val Pro
        50                  55                  60 gac agg ttc agt ggc agt ggg tca gga act gct ttc aca ctg aga atc    240
Asp Arg Phe Ser Gly Ser Gly Ser Gly Thr Ala Phe Thr Leu Arg Ile
65                  70                  75                  80 agt aga gtg gag gct gag gat gtg ggt gtt tat tac tgt atg caa cat    288
Ser Arg Val Glu Ala Glu Asp Val Gly Val Tyr Tyr Cys Met Gln His
                85                  90                  95 cta gaa tat cca ttc acg ttc ggc tcg ggg aca aag ttg gaa ata aaa    336
Leu Glu Tyr Pro Phe Thr Phe Gly Ser Gly Thr Lys Leu Glu Ile Lys
                100                 105                 110 cgg                                                                339
Arg
```

<210> SEQ ID NO 20
<211> LENGTH: 113
<212> TYPE: PRT
<213> ORGANISM: Mus sp.

<400> SEQUENCE: 20

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Val Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
                100                 105                 110

Arg
```

<210> SEQ ID NO 21

```
<211> LENGTH: 48
<212> TYPE: DNA
<213> ORGANISM: Mus sp.
<220> FEATURE:
<221> NAME/KEY: CDS
<222> LOCATION: (1)..(48)

<400> SEQUENCE: 21 agg tct agt aag agt ctc ctg cat agt aat ggc aac act tac ttg tat     48
Arg Ser Ser Lys Ser Leu Leu His Ser Asn Gly Asn Thr Tyr Leu Tyr
1               5                   10                  15

<210> SEQ ID NO 22
<211> LENGTH: 16
<212> TYPE: PRT
<213> ORGANISM: Mus sp.

<400> SEQUENCE: 22

Arg Ser Ser Lys Ser Leu Leu His Ser Asn Gly Asn Thr Tyr Leu Tyr
1               5                   10                  15

<210> SEQ ID NO 23
<211> LENGTH: 21
<212> TYPE: DNA
<213> ORGANISM: Mus sp.
<220> FEATURE:
<221> NAME/KEY: CDS
<222> LOCATION: (1)..(21)

<400> SEQUENCE: 23 cgg atg tcc aac ctt gcc tca                                         21
Arg Met Ser Asn Leu Ala Ser
1               5

<210> SEQ ID NO 24
<211> LENGTH: 7
<212> TYPE: PRT
<213> ORGANISM: Mus sp.

<400> SEQUENCE: 24

Arg Met Ser Asn Leu Ala Ser
1               5

<210> SEQ ID NO 25
<211> LENGTH: 63
<212> TYPE: DNA
<213> ORGANISM: Mus sp.
<220> FEATURE:
<221> NAME/KEY: CDS
<222> LOCATION: (1)..(63)

<400> SEQUENCE: 25 gta gga ggg att aac ttt tct atg gac tac tgg ggt caa gga acc tca     48
Val Gly Gly Ile Asn Phe Ser Met Asp Tyr Trp Gly Gln Gly Thr Ser
1               5                   10                  15 gtc acc gtc tcc tca                                                 63
Val Thr Val Ser Ser
            20

<210> SEQ ID NO 26
<211> LENGTH: 21
<212> TYPE: PRT
<213> ORGANISM: Mus sp.

<400> SEQUENCE: 26

Val Gly Gly Ile Asn Phe Ser Met Asp Tyr Trp Gly Gln Gly Thr Ser
1               5                   10                  15
```

```
Val Thr Val Ser Ser
            20

<210> SEQ ID NO 27
<211> LENGTH: 39
<212> TYPE: DNA
<213> ORGANISM: Mus sp.
<220> FEATURE:
<221> NAME/KEY: CDS
<222> LOCATION: (1)..(39)

<400> SEQUENCE: 27 tgg acg ttc ggt gga ggc acc aag ctg gaa atc aaa cgg        39
Trp Thr Phe Gly Gly Gly Thr Lys Leu Glu Ile Lys Arg
1               5                   10

<210> SEQ ID NO 28
<211> LENGTH: 13
<212> TYPE: PRT
<213> ORGANISM: Mus sp.

<400> SEQUENCE: 28

Trp Thr Phe Gly Gly Gly Thr Lys Leu Glu Ile Lys Arg
1               5                   10

<210> SEQ ID NO 29
<211> LENGTH: 63
<212> TYPE: DNA
<213> ORGANISM: Mus sp.
<220> FEATURE:
<221> NAME/KEY: CDS
<222> LOCATION: (1)..(63)

<400> SEQUENCE: 29 tgg ggt tac gac agg gag tgg ttt gct tac tgg ggc caa ggg act ctg        48
Trp Gly Tyr Asp Arg Glu Trp Phe Ala Tyr Trp Gly Gln Gly Thr Leu
1               5                   10                  15 gtc act gtc tct gca                                                    63
Val Thr Val Ser Ala
            20

<210> SEQ ID NO 30
<211> LENGTH: 21
<212> TYPE: PRT
<213> ORGANISM: Mus sp.

<400> SEQUENCE: 30

Trp Gly Tyr Asp Arg Glu Trp Phe Ala Tyr Trp Gly Gln Gly Thr Leu
1               5                   10                  15

Val Thr Val Ser Ala
            20

<210> SEQ ID NO 31
<211> LENGTH: 39
<212> TYPE: DNA
<213> ORGANISM: Mus sp.
<220> FEATURE:
<221> NAME/KEY: CDS
<222> LOCATION: (1)..(39)

<400> SEQUENCE: 31 ttc acg ttc ggc tcg ggg aca aag ttg gaa ata aaa cgg        39
Phe Thr Phe Gly Ser Gly Thr Lys Leu Glu Ile Lys Arg
1               5                   10

<210> SEQ ID NO 32
<211> LENGTH: 13
```

```
<212> TYPE: PRT
<213> ORGANISM: Mus sp.

<400> SEQUENCE: 32

Phe Thr Phe Gly Ser Gly Thr Lys Leu Glu Ile Lys Arg
1               5                   10

<210> SEQ ID NO 33
<211> LENGTH: 12
<212> TYPE: PRT
<213> ORGANISM: Mus sp.

<400> SEQUENCE: 33

Leu Met Lys Asn Met Asp Pro Leu Asn Asp Asn Val
1               5                   10

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other

<400> SEQUENCE: 34
ytnatgaara ayatggaycc nytnaaygay aaygtn                                36

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Gly Ser Gly Gly Gly Gly Ser Gly Gly Gly Gly Ser
1               5                   10                  15
```